United States Patent
Mousa

(10) Patent No.: US 9,597,351 B2
(45) Date of Patent: Mar. 21, 2017

(54) NANO-TARGETED DELIVERY OF PROTEASE, POLYMERASE INHIBITORS WITH OR WITHOUT IMMUNE MODULATORS IN THE TREATMENT OF HEPATITIS C

(71) Applicant: Shaker A. Mousa, Wynantskill, NY (US)

(72) Inventor: Shaker A. Mousa, Wynantskill, NY (US)

( * ) Notice: Subject to any disclaimer, the term of this patent is extended or adjusted under 35 U.S.C. 154(b) by 34 days.

(21) Appl. No.: 14/614,496

(22) Filed: Feb. 5, 2015

(65) Prior Publication Data
US 2015/0224134 A1 Aug. 13, 2015

Related U.S. Application Data

(60) Provisional application No. 61/936,944, filed on Feb. 7, 2014.

(51) Int. Cl.

| | | |
|---|---|---|
| A61K 31/353 | (2006.01) | |
| A61K 31/7056 | (2006.01) | |
| A61K 31/7072 | (2006.01) | |
| A61K 31/198 | (2006.01) | |
| A61K 31/737 | (2006.01) | |
| A61K 45/06 | (2006.01) | |
| A61K 31/726 | (2006.01) | |
| A61K 31/728 | (2006.01) | |
| A61K 31/734 | (2006.01) | |
| A61K 31/7032 | (2006.01) | |
| A61K 9/00 | (2006.01) | |
| A61K 9/16 | (2006.01) | |
| A61K 9/20 | (2006.01) | |

(52) U.S. Cl.
CPC .......... *A61K 31/737* (2013.01); *A61K 31/198* (2013.01); *A61K 31/353* (2013.01); *A61K 31/7056* (2013.01); *A61K 31/7072* (2013.01); *A61K 31/728* (2013.01); *A61K 31/734* (2013.01); *A61K 45/06* (2013.01)

(58) Field of Classification Search
None
See application file for complete search history.

(56) References Cited

U.S. PATENT DOCUMENTS

2014/0017329 A1   1/2014   Mousa

OTHER PUBLICATIONS

Kumar, Development and Characterization of Ribavirin Loaded Poly(Lactide-Co-Glycolide) Nanoparticles by Double Emulsification Method, Thesis, Jadavpur Universityk, 2012-13.*
Gane, N Engl J Med 368;1, Jan. 3, 2013.*
Dhiman, Journal of Clinical and Experimental Hepatology, Dec. 2011, vol. 1, No. 3, 159-160.*
Pritee S. Mahajan, Kishor B Mahajan and A. B. Darekar, "A Review on Solid Lipid Nanoparticle (SLN): An Advanced Treatment Modality", 13 pages, International Journal of Pharmaceutical Sciences and Research, retrieved on Aug. 5, 2016 from the Internet: <URL: http://ijpsr.com/bft-article/a-review-on-solid-lipid-nanoparticle-sln-an-advanced-treatment-modality/?view=fulltext >.
PCT ISR WO; PCT/US2016/014795; Mar. 31, 2016, 8 pages.
Belousova, Vet al. Recent Advances and Future Directions in the Management of Hepatitis C Infections. Pharmacology & Therapeutics. 2015 (available online Sep. 2014). vol. 145, p. 96, first column, third-fourth paragraphs; p. 99, second column, fifth-sixth paragraphs, 11 pages.
Ozgur, E et al. Mobile Phone Radiation-Induced Free Radical Damage in the liver is Inhibited by the Antioxidants N-Acetyl Cysteine and Epigallocatechin-Gallate. International Journal of Radiation Biology. Nov. 2010. vol. 86, No. 11; p. 936, first column, second-third paragraphs; p. 942; second column, third paragraph, 12 pages.
Sudha, T et al. Suppression of Pancreatic Cancer by Sulfated Non-Anticoagulant Low Molecular Weight Heparin. Cancer Letters. Aug. 1, 2014 vol. 350, No. O; p. 2, third-fourth paragraphs; p. 8, fifth paragraph, 20 pages.
Xu, X et al. Heparin: An Intervenor in Cell Communications. Journal of Cellular and Molecular Medicine. 2010. vol. 14, No. 1-2; p. 176, second column, second paragraph, 6 pages.
Wang, Wet al. Galactosylated Solid Lipid Nanoparticles with Cucurbitacin B Improves the liver Targetability. Drug Delivery. 2010. vol. 17, No. 3; abstract, 2 pages.

* cited by examiner

*Primary Examiner* — Layla Berry
(74) *Attorney, Agent, or Firm* — Schmeiser, Olsen & Watts, LLP

(57) ABSTRACT

This disclosure concerns novel formulation and Nanoformulations as defined in the specification and compositions comprising combination of HCV protease and polymerase inhibitors, with or without interferon, along with anti-fibrotic/anti-hemolytic agents' combination of naturally driven Polyphenol/Thiols, and Non-anticoagulant GAGs. These compounds are effective antiviral agents, especially in inhibiting the function of the various genotypes of Hepatitis C virus (HCV). Thus, the disclosure also concerns a method of treating HCV related diseases or conditions by use of these novel compounds or a composition comprising nano-targeted delivery of novel nanoformulation containing combined composition for HCV and/or hepatic targeted delivery for improved efficacy and safety.

21 Claims, 16 Drawing Sheets

NANO-TARGETED DELIVERY OF PROTEASE, POLYMERASE INHIBITORS WITH OR WITHOUT IMMUNE MODULATORS IN THE TREATMENT OF HEPATITIS C

RELATED APPLICATION

The present invention claims priority to U.S. Provisional No. 61/936,944, filed on Feb. 7, 2014, which is incorporated herein by reference in its entirety.

FIELD OF THE INVENTION

The present invention provides a nanoformulation and HCV and/or liver targeting of antiviral compounds in the treatment of Hepatitis C.

BACKGROUND

The severe health conditions associated with chronic HCV infection remain a global concern. The most effective therapy at present for HCV is the combination therapy of PEGylated interferon (IFN) γ (PEG-IFNγ) and ribavirin. This combination therapy involves multiple doses of PEG-IFNγ and ribavirin, and takes more than 48 weeks for completion; however, the success rate is only around 50%. In addition, the cost of IFNγ combination therapy is high, efficiency is low and the therapy has serious side effects including fever and hemolytic anemia. Various polymerase inhibitors demonstrated significant anti-HCV efficacy against the different sub-types but associated with serious adverse effects and excessive cost. Therefore, there is an urgent need for targeted antiviral agents for the treatment of HCV infection.

It is estimated that over 300 million people (1) are infected with Hepatitis C virus (HCV) worldwide. Africa and the Eastern Mediterranean region have the highest documented infection rates, and Egypt has the highest infection rate for a single country in the world. In the United States, an estimated 4.1 million people are infected with HCV, representing approximately 1.8% of the population) (2). Of these 4.1 million HCV-infected individuals, approximately 3.2 million have chronic Hepatitis C infection, and can therefore potentially spread HCV to others. Because of the low survival rate (~50%) (3) of individuals with Hepatitis C and the high cost of treatment, Hepatitis C continues to be one of the most dangerous diseases in the world. It is therefore imperative to develop a novel, safe and effective formulation for the treatment of this disease that can quickly move into the clinical phase.

SUMMARY OF THE INVENTION

The present invention provides a composition, comprising: a formulated or Nanoformulated polymerase inhibitor; and a protease inhibitor, with anti-fibrotic/anti-hemolytic agents, along with hepatic and/or HCV targeting

DETAILED DESCRIPTION OF THE INVENTION

Figure 1:
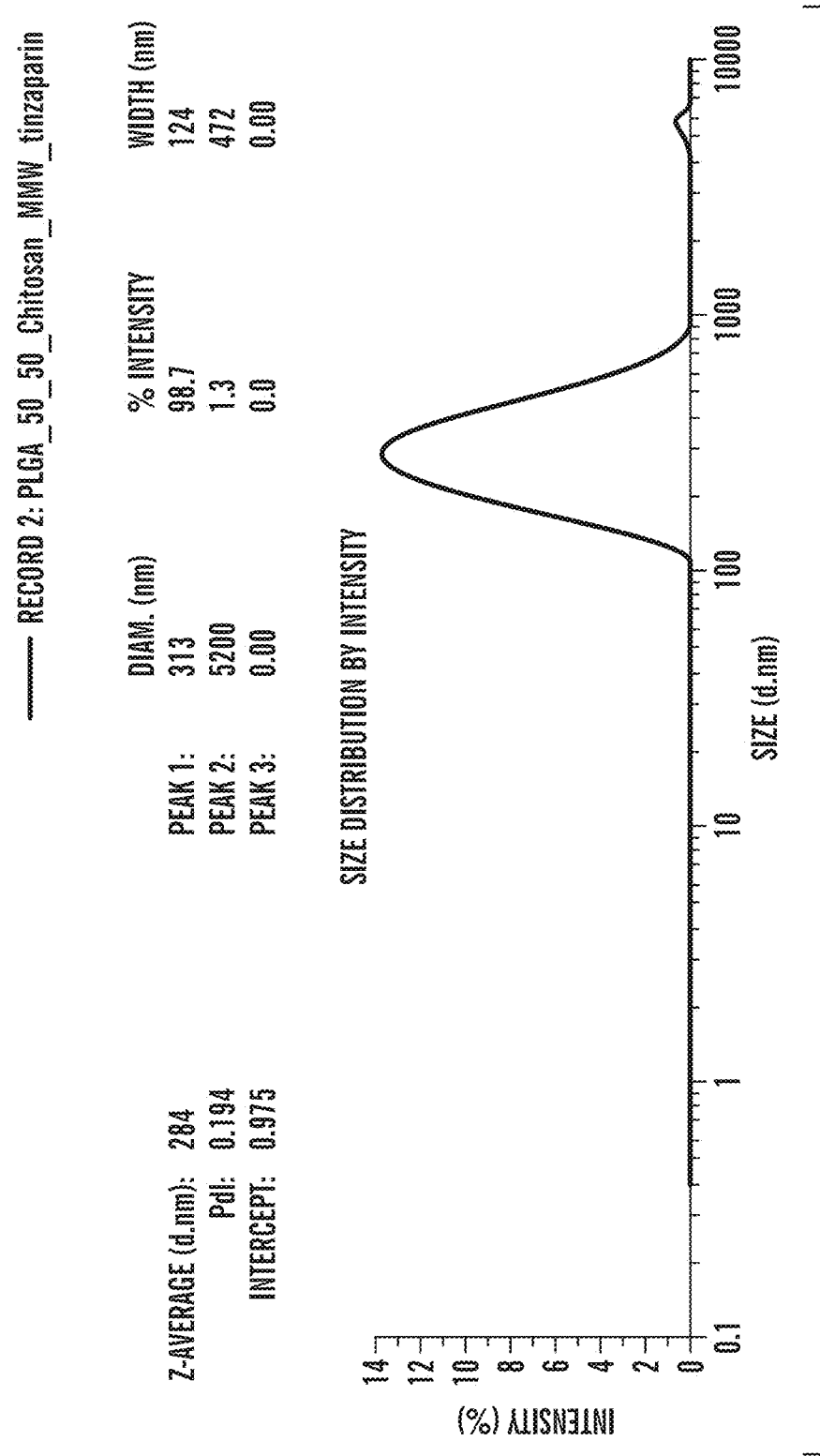
FIG. 1 depicts Size measurement of chitosan grafted PLGA nanoparticles by DLS, in accordance with embodiments of the present invention.
Figure 1:
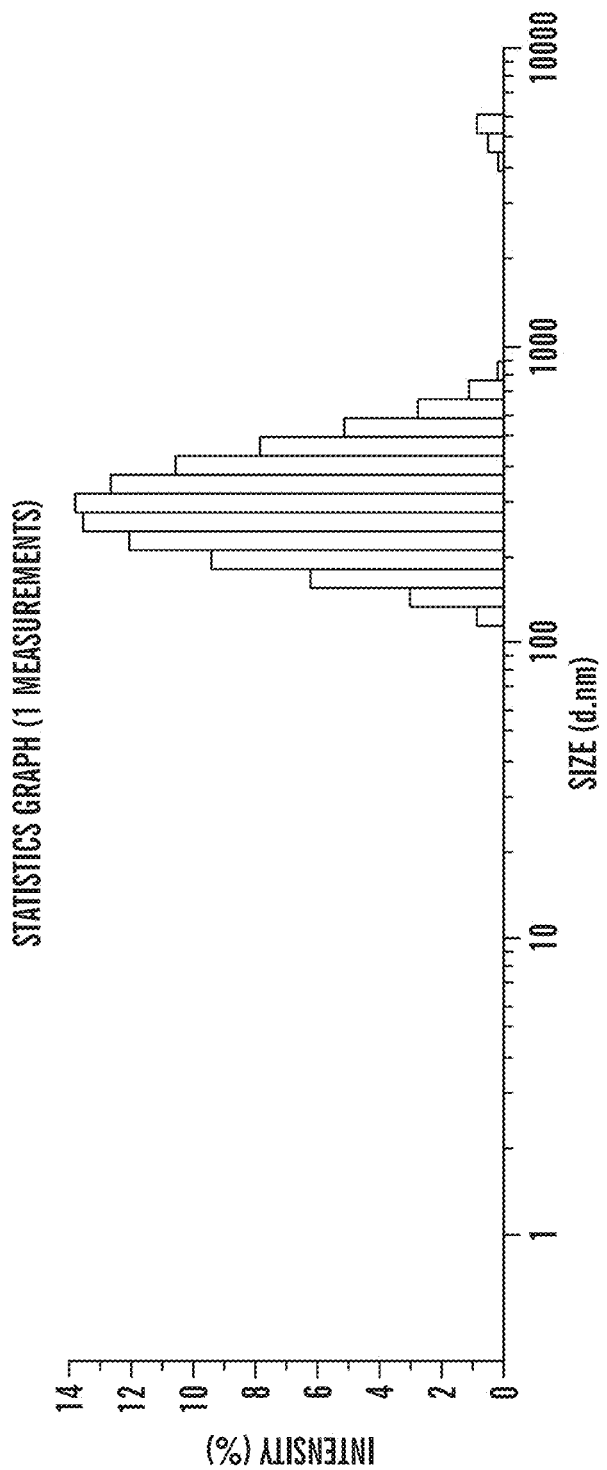

The use of PEGylated IFN γ with ribavirin has serious side effects and a significant proportion of patients infected with HCV have an unsatisfactory outcome with this therapy. Major advances have been realized in the development of specific non-nucleoside inhibitors of the viral NS5B RNA-dependent RNA polymerase. Clinical proof-of-concept for allosteric non-nucleoside HCV polymerase inhibitors has been reported and several compounds have progressed into preclinical and clinical studies. It is likely that in the future NS5B inhibitors were form an integral part of more effective anti-HCV therapies, combining the use of small-molecule antiviral drugs with or without the assistance of immune modulators such as IFNs. The combination of protease inhibitor such as ribavirin (Compound A) in the presence of anti-fibrotic/anti-hemolytic agents, and with the polymerase inhibitor would result in synergistic effects and minimize the emergence of resistance. This invention combines known polymerase inhibitor such as (Compound A) Isopropyl (2S)-2-[(2R, 3R, 4R, 5R)-5-(2, 4-dioxopyrimidin-1-yl)-4-fluoro-3-hydroxy-4-methyl-tetrahydrofuran-2-yl] methoxy-phenoxy-phosphoryl] amino] propionate with known protease inhibitor such as (Compound B) 1-[(2R,3R,4S,5R)-3,4-dihydroxy-5-(hydroxymethyl)oxolan-2-yl]-1H-1,2,4-triazole-3-carbox amide at 400 mg and 1000 mg in a solid dosage form, respectively in combinations with anti-fibrotic/anti-hemolytic agents (Compound C). Anti-fibrotic/anti-hemolytic agents that protect against live fibrosis and hemolytic anemia-induced by ribavirin would include the following naturally driven polyphenols (Resveratrol, Catechin epigallocatechin gallate (EGCG), Eligic acid, punicagilin, and other polyphenols) and thiols (allin, N-acetyl cysteine, glutathione, and other thiols). Additionally, polyanionic non-anticoagulant glycosaminoglycans such as non-anticoagulant Low Molecular Weight Heparins (NACH), heparan, dermatan, and other non-anticoagulant GAGs (Compound D) that bind and sequester Hepatitis C Virus lowering viral load would also be co-encapsulated or combined with compounds A, B, and C.

It is imperative that a new sensitive, cost effective, safe and efficient technology is developed in order to overcome this silent killer. The application of nanotechnology in medicine provides unprecedented opportunities for addressing many of the current gaps in clinical diagnosis and therapy. Potential applications of this cutting edge technology could have a revolutionary impact on the treatment of Hepatitis C. In the past few decades, the development of controlled release systems based on nanoparticles that permit a sustained or pulsed release of encapsulated drug (including (IFN) γ has attracted much interest. Polymeric particles are of particular interest, as they are more stable and permit administration by the parenteral route (subcutaneous) as well as oral route as tablet, chewable tablet or capsule. Furthermore, it is well known that nanoparticulate carriers not only have the potential to incorporate multiple drugs (either by encapsulation or chemical conjugation), but also have tremendous potential for a targeted delivery. Keeping this mind, we developed a polymeric nanoparticle-based technology platforms incorporating the protease inhibitor ribavirin or taribavirin with or without IFNγ and various types of polymerase inhibitors in the treatment of Hepatitis C, along with anti-fibrotic/anti-hemolytic agents, In addition, we propose to conjugate a therapeutic peptide, p14 (NS3 peptide), that were confer the ability to target viral NS3 helicase, which is anticipated to increase the efficacy of the drugs encapsulated into the nanoparticle platforms. Additionally, we also propose that these drug loaded nanoparticles were attached to a monoclonal antibody (FAb fragments) directed against epitopes conserved on HCV surface E2 glycoprotein of genotypes 1a, 1b, 2a, 2b and 4. Thus, the incorporation of protease inhibitor such as Compound A and polymerase inhibitors (Compound B) along with anti-fibrotic/anti-hemolytic agents (Compound C), and Non-anticoagulant GAGs (Compound D) inside the nanoparticle would allow for optimal anti-viral efficacy and optimal safety profiles. At the same time, targeted delivery through p14 conjugation and combination therapy with incorporation of taribavirin or ribavirin in the same nanoparticle is expected to increase the efficacy of the formulation via targeted delivery to HCV and/or the liver. This invention accomplished through the following aims:

Aim 1: Synthesis and characterization of different nanoformulations incorporating Protease inhibitor such as Compound A (ribavirin), polymerase inhibitors such as Compound B (sofosbuvir) with or without IFNγ, along with anti-fibrotic/anti-hemolytic such as Compound C (polyphenol/thiol), and Non-anticoagulant GAGs such as Compound D (NACH, Oligosaccharide, dermatan sulfate, . . . ).

Aim 2: Determine the efficacy of the nanoformulation in cells in vitro using confocal imaging and qualitative in vitro anti-HCV screening;

Aim 3: Determine the efficacy of selected nanoformulations in vivo using chimeric urokinase-type plasminogen activator (uPA)-severe combined immunodeficiency (SCID) (uPA-SCID) mice engrafted with human hepatocytes.

The following formulations and nanoformulations were derived:

1—Solid dosage form combining protease inhibitor such as Compound A Ribavirin (1-[(2R,3R,4S,5R)-3,4-dihydroxy-5-(hydroxymethyl) oxolan-2-yl]-1H-1,2,4-triazole-3-carboxamide at 500-1000 mg/tablet or capsule in sustained release formulation plus polymerase inhibitor such as Compound B Sofosbuvir (Isopropyl (2S)-2-[(2R,3R,4R,5R)-5-(2,4-dioxopyrimidin-1-yl)-4-fluoro-3-hydroxy-4-methyl-tetrahydrofuran-2-yl]methoxy-phenoxyphosphoryl]amino] propionate) at 200-400 mg/tablet, chewable tablet or capsule, along with anti-fibrotic/anti-hemolytic agents combination of naturally driven Polyphenol/Thiols (Compound C), and Non-anticoagulant GAGs (Compound D inside the nanoparticle would allow for optimal anti-viral efficacy and optimal safety profiles.

2—Nanoformulation containing Ribavirin (100-200 mg) and Sofosbuvir (40-100 mg), along with anti-fibrotic/anti-hemolytic agents' combination of naturally driven Polyphenol/Thiols (Compound C), and Non-anticoagulant GAGs (Compound D) in solid lipid nanoparticles, PLGA-PEG nanoparticles, Chitosan-fatty acid, Chitosan-PLGA, Chitosan-Hyaluronic acid coated with Lactobionic, glycyrrhizin and/or galactosylated for hepatic targeting.

3—Nanoformulation containing Ribavirin (100 mg) and Sofosbuvir (40 mg) and lower doses in solid lipid nanoparticles, PLGA-PEG nanoparticles, Chitosan-fatty acid, Chitosan-PLGA, Chitosan-Hyaluronic acid, along with anti-fibrotic/anti-hemolytic agents' combination of naturally driven Polyphenol/Thiols (Compound C), and Non-anticoagulant GAGs (Compound D) and conjugated with αvβ3 integrin ligand and/or p14 peptide (NS3 peptide) for HCV targeting.

4—Nanoformulation containing Ribavirin (10-20 mg) and Sofosbuvir (4-10 mg) in solid lipid nanoparticles, PLGA-PEG nanoparticles, Chitosan-fatty acid, Chitosan-PLGA, Chitosan-Hyaluronic acid, along with anti-fibrotic/anti-hemolytic agents' combination of naturally driven Polyphenol/Thiols (Compound C), and Non-anticoagulant GAGs (Compound D) and conjugated with αvβ3 integrin ligand and/or p14 peptide (NS3 peptide) for HCV targeting and coated or conjugated with Lactobionic, glycyrrhizin and/or galactosylated for hepatic targeting.

The application of nanotechnology in medicine provides unprecedented opportunities for addressing many of the current gaps in the diagnosis and therapy. Potential applications of this cutting edge technology could have a revolutionary impact on the treatment of Hepatitis C. In last few decades, the development of controlled release systems based on nanoparticles that permit a sustained or pulsed release of encapsulated drug has attracted much interest. Polymeric particles are especially interesting as they are more stable and permit administration by the parenteral route as well as oral route. Furthermore, it is well known that nanoparticulate carriers not only have the potential to incorporate multiple drugs (either by encapsulation or chemical conjugation), but also have the tremendous potential for targeted delivery. Many studies have documented that custom-synthesized nanoparticles accumulate in the liver. Proper delivery of antiviral drugs to the HCV and/or the liver, is a prerequisite for efficient Hepatitis C treatment. Thus, nanoparticles could provide the added advantage of delivering drugs into the liver effectively, thereby increasing the efficacy of the drugs. Importantly, nanoparticulate carrier systems can be fluorescently labeled with different dyes, which enable investigation of the pathways and accumulation of nano-carriers in real time. Tracking of the Nano-carriers allowed identification of mechanistic pathways of localization and activity, thereby providing the basis for optimized formulations for better results. Conjugation of a therapeutic peptide, such as p14 (NS3 peptide), that has the ability to target viral NS3 helicase increase the efficacy of nano-encapsulated drugs. Monoclonal antibodies (Fab fragments) or TAT peptide targeting HCV also can be useful for efficient targeted delivery vehicles that can be conjugated on the surface of the drug loaded nanoparticles with protease and RNA polymerase inhibitor, with or without interferon.

One of the effective therapy for Hepatitis C is combination therapy using PEGylated IFN γ (PEG-IFNγ) and ribavirin. This combination therapy involved multiple doses of PEG-IFN and ribavirin and takes more than 48 weeks to complete. However, the success rate is only around 50%. In addition, the cost of IFNγ combination therapy is high, efficiency is low, and the therapy has serious side effects. It is therefore imperative to develop novel, sensitive, cost effective, safe and efficient technologies that can effectively overcome this silent killer. With this in mind, we developed polymeric nanoparticle-based technology antiviral drug for the treatment of Hepatitis C. Conjugation of a therapeutic peptide, p14 (NS3 peptide), that has the ability to target viral NS3 helicase, is also used in order to increase the efficacy of the drugs. Incorporation of IFN γ inside the nanoparticles expected to reduce IFNγ-related toxicity; at the same time, targeted delivery through p14 conjugation and combination therapy using the relatively less toxic tarivabirin (as compared to conventional ribavirin) incorporated into the same nanoparticles increased the efficacy of the formulation. Furthermore, conjugation of Monoclonal antibodies (Fab fragments) or TAT peptide targeting HCV, on the surface of the drug loaded nanoparticles can be highly efficient and can be used for the treatment most of the types of the HCV including genotype 1a, 1b, 2a, 2b, 4 etc.

FIG. 1 depicts Size measurement of chitosan grafted PLGA nanoparticles by DLS, in accordance with embodiments of the present invention.

FIG. 2 depicts Confocal imaging of HepG2 cell showing the uptake of Cy3-labeled chitosan grafted PLGA nanoparticles, in accordance with embodiments of the present invention.

FIG. 3 depicts Schematic diagram showing conjugation strategy for linking monoclonal antibody/TAT Peptide/p14 peptide (NS3 peptide) nanoparticles, in accordance with embodiments of the present invention.

FIG. 4 depicts A sketch illustrating the Design of Solid lipid nanoparticles (SLN) for drug delivery—Nanoformulation are synthesized for the encapsulation of protease and polymerase inhibitors with or without interferon, with anti-fibrotic/anti-hemolytic agents' combination of naturally driven Polyphenol/Thiols, and Non-anticoagulant GAGs, along with targeting for hepatic cells using Lactobionic acid, glycyrrhizin, and/or Galactosylated, in accordance with embodiments of the present invention.

FIG. 5 depicts A sketch illustrating the Design of Solid lipid nanoparticles (SLN) for drug delivery—Nanoformulation are synthesized for the encapsulation of polymerase and protease inhibitors with or without interferon, with anti-fibrotic/anti-hemolytic agents' combination of naturally driven Polyphenol/Thiols, and Non-anticoagulant GAGs, and along with targeting for hepatitis C virus can be targeted by conjugation of high affinity v 3 ligand and coating/conjugation for hepatic cells using Lactobionic acid, glycyrrhizin, and/or Galactosylated, in accordance with embodiments of the present invention.

FIG. 6 depicts A sketch illustrating the Design of nanoparticles for drug delivery—Nanoformulation are synthesized for the encapsulation of polymerase and protease inhibitors with or without interferon, with anti-fibrotic/anti-hemolytic agents' combination of naturally driven Polyphenol/Thiols, and Non-anticoagulant GAGs, and along with targeting for hepatic cells using coating/conjugation with Lactobionic acid, glycyrrhizin, and/or Galactosylated, in accordance with embodiments of the present invention.

Figure 7:
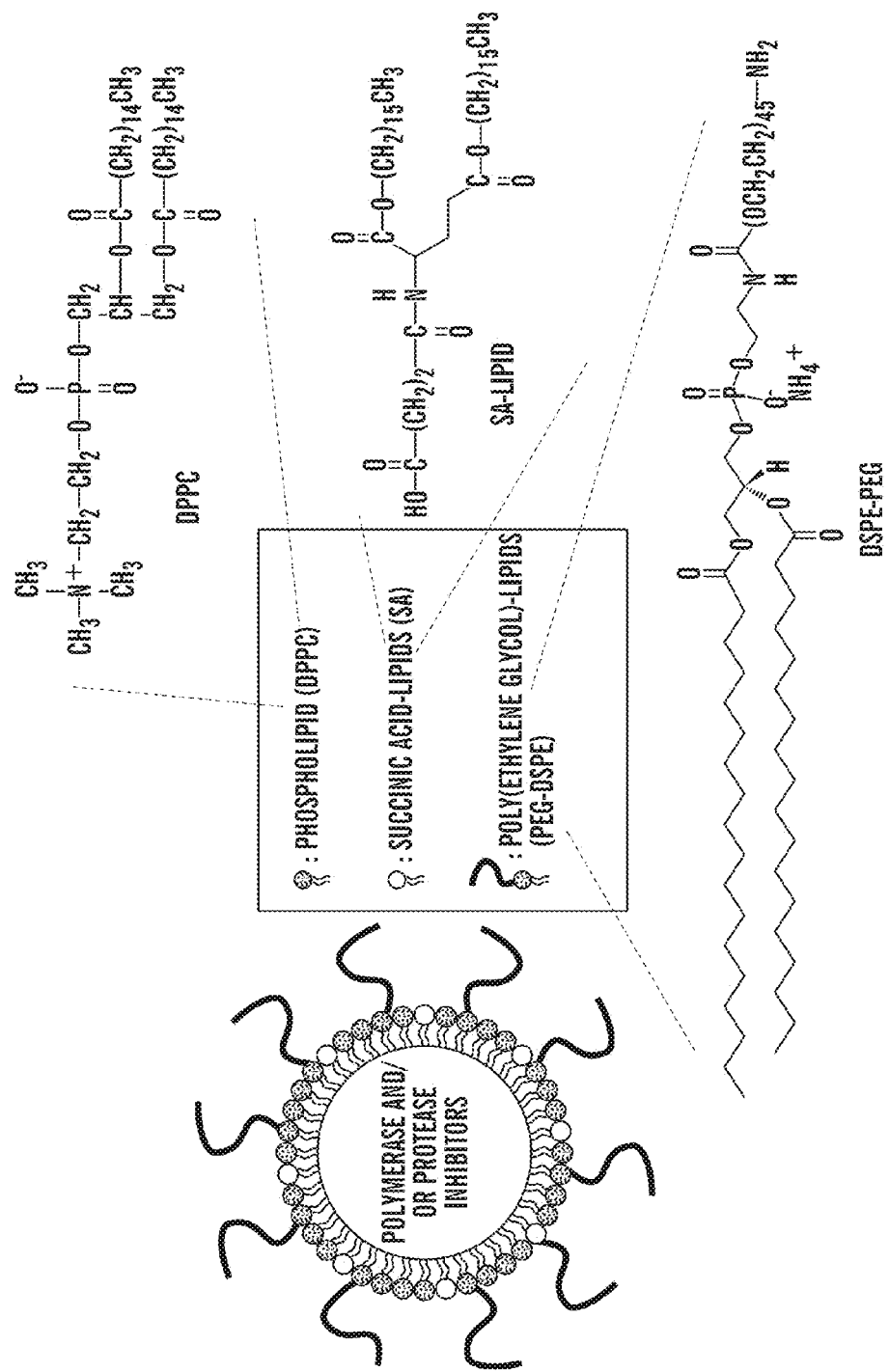
FIG. 7 depicts A sketch illustrating the Design of nanoparticles for drug delivery—Nanoformulation are synthesized for the encapsulation of polymerase and protease inhibitors with or without interferon, containing anti-fibrotic/anti-hemolytic agents, and along with targeting for hepatic cells using coating/conjugation with Lactobionic acid, glycyrrhizin, and/or Galactosylated, in accordance with embodiments of the present invention.

FIG. 7 depicts A sketch illustrating the Design of nanoparticles for drug delivery—Nanoformulation are synthesized for the encapsulation of polymerase and protease inhibitors with or without interferon, with anti-fibrotic/anti-hemolytic agents' combination of naturally driven Polyphenol/Thiols, and Non-anticoagulant GAGs, and along with targeting for hepatic cells using coating/conjugation with Lactobionic acid, glycyrrhizin, and/or Galactosylated, in accordance with embodiments of the present invention.

Figure 8:
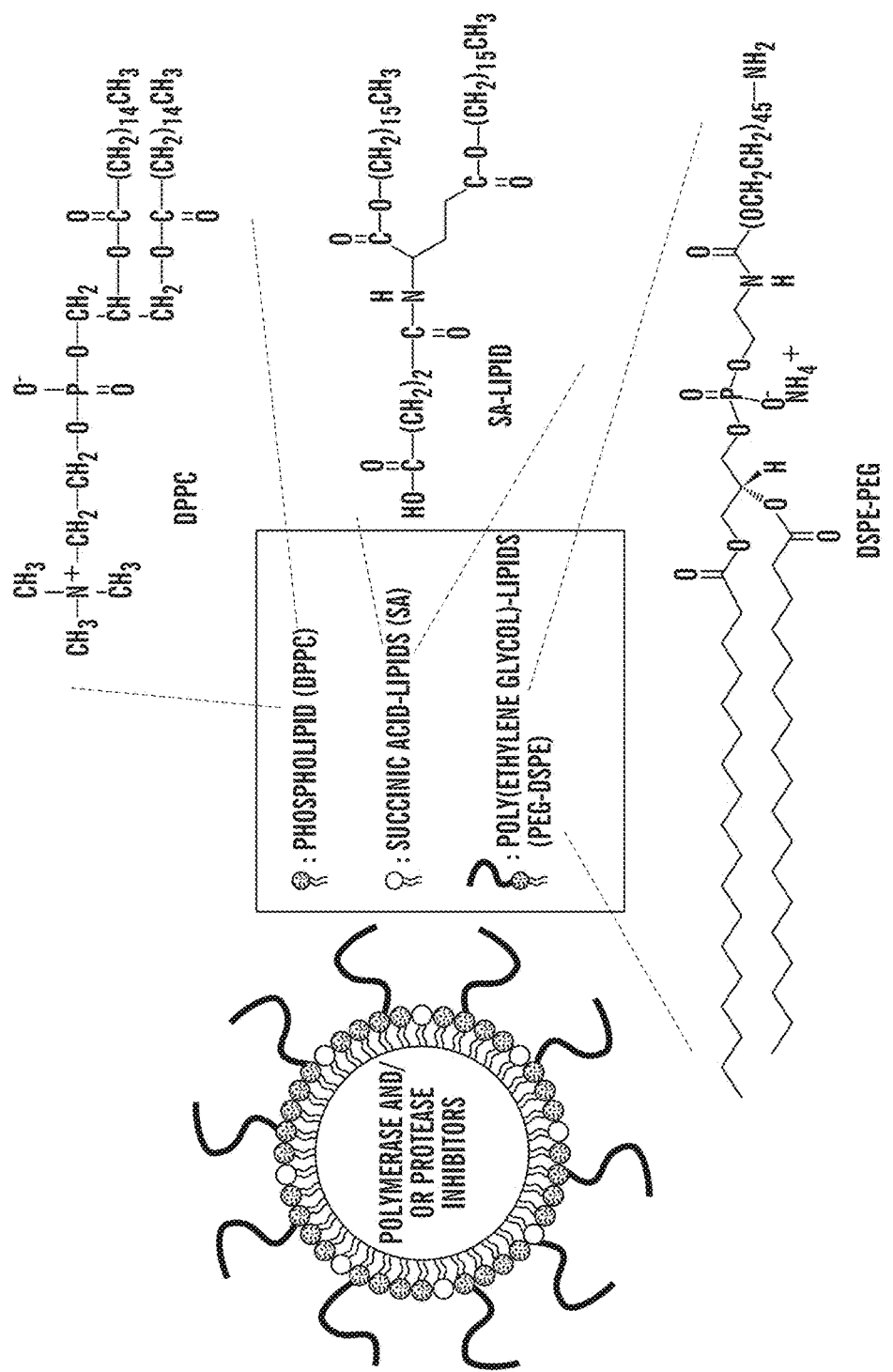
FIG. 8 depicts A sketch illustrating the Design of nanoparticles for drug delivery—Nanoformulation are synthesized for the encapsulation of polymerase and protease inhibitors with or without interferon, containing anti-fibrotic/anti-hemolytic agents, and along with targeting for hepatic cells using coating/conjugation with Lactobionic acid, glycyrrhizin, and/or Galactosylated, in accordance with embodiments of the present invention.

FIG. 8 depicts A sketch illustrating the Design of nanoparticles for drug delivery—Nanoformulation are synthesized for the encapsulation of polymerase and protease inhibitors with or without interferon, with anti-fibrotic/anti-hemolytic agents' combination of naturally driven Polyphenol/Thiols, and Non-anticoagulant GAGs, and along with targeting for hepatic cells using coating/conjugation with Lactobionic acid, glycyrrhizin, and/or Galactosylated, in accordance with embodiments of the present invention.

Figure 9:
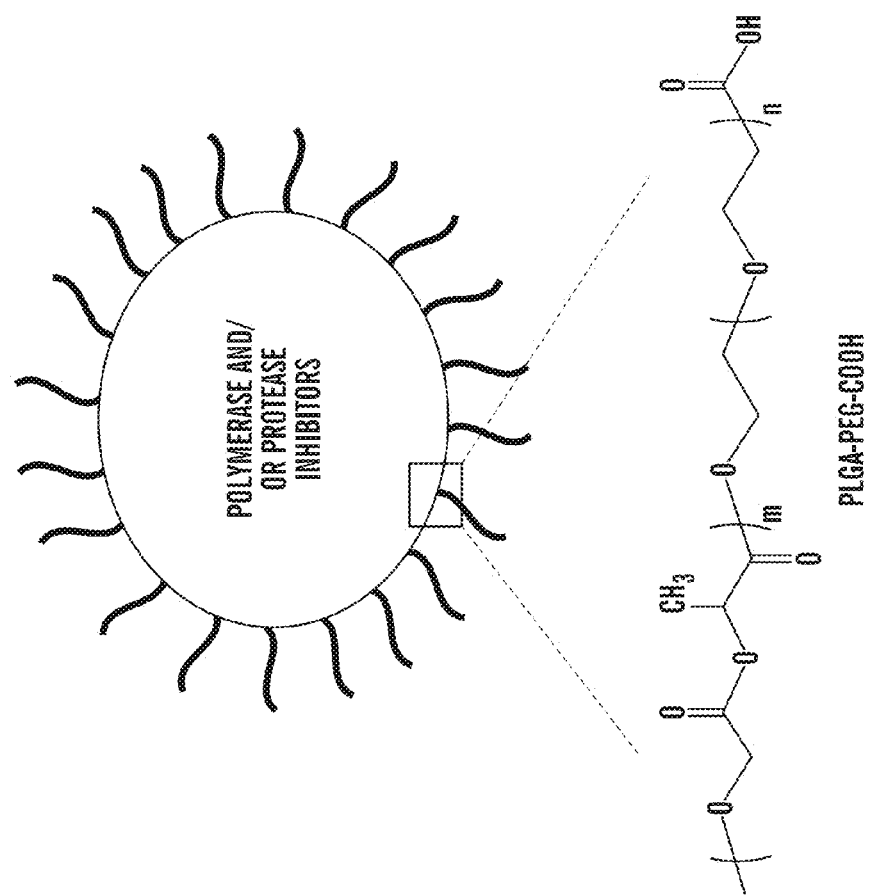
FIG. 9 depicts A sketch illustrating the Design of PLGA-PEG nanoparticles for drug delivery—Nanoformulation are synthesized for the encapsulation of polymerase and protease inhibitors with or without interferon, containing anti-fibrotic/anti-hemolytic agents, and along with targeting for hepatic cells using coating/conjugation with Lactobionic acid, glycyrrhizin, and/or Galactosylated, in accordance with embodiments of the present invention.

FIG. 9 depicts A sketch illustrating the Design of PLGA-PEG nanoparticles for drug delivery—Nanoformulation are synthesized for the encapsulation of polymerase and protease inhibitors with or without interferon, with anti-fibrotic/anti-hemolytic agents' combination of naturally driven Polyphenol/Thiols, and Non-anticoagulant GAGs, and along with targeting for hepatic cells using coating/conjugation with Lactobionic acid, glycyrrhizin, and/or Galactosylated, in accordance with embodiments of the present invention.

Figure 10:
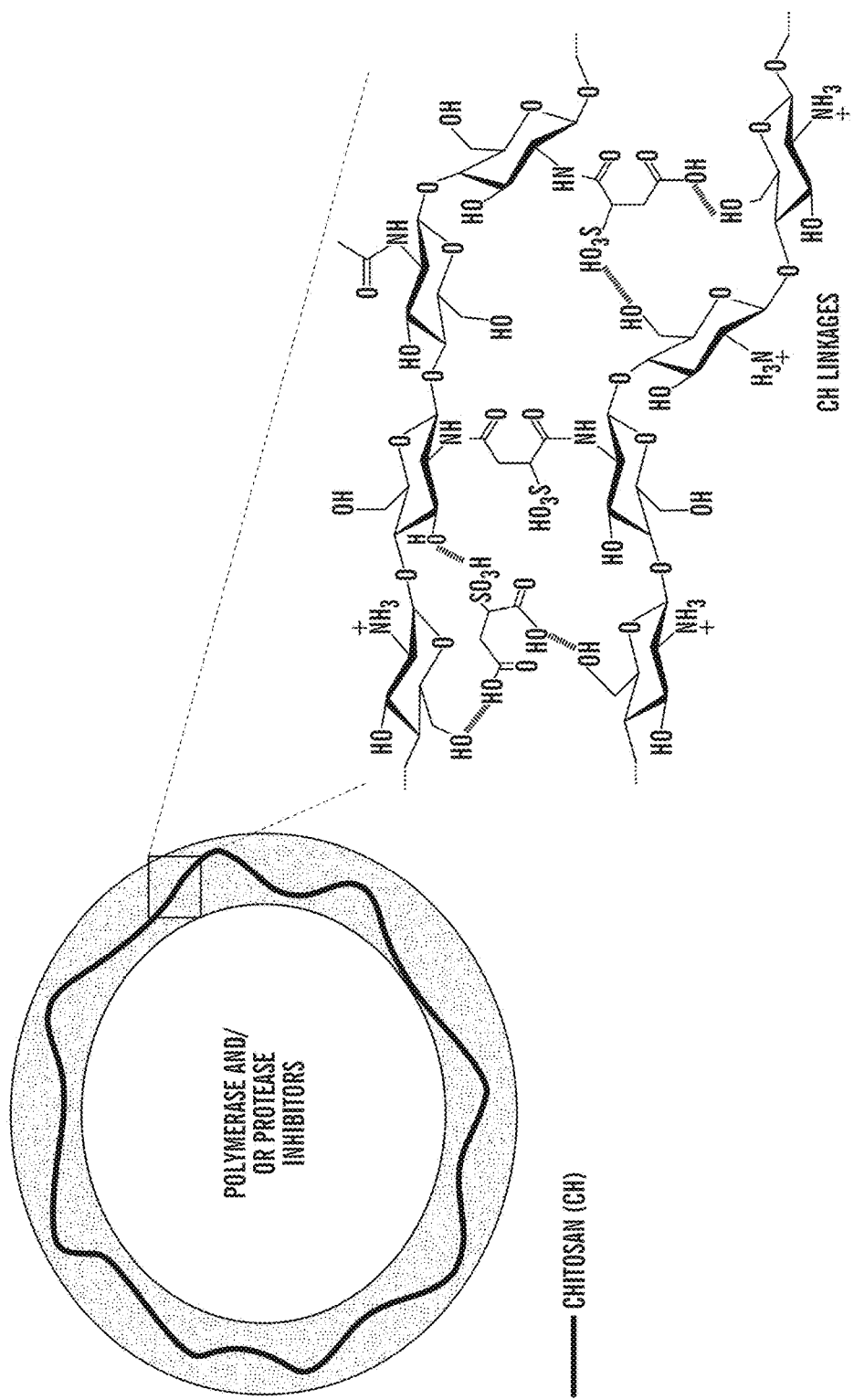
FIG. 10 depicts A sketch illustrating the Design of cross-linked Chitosan nanoparticles for drug delivery—Nanoformulation are synthesized for the encapsulation of polymerase and protease inhibitors with or without interferon, containing anti-fibrotic/anti-hemolytic agents, and along with targeting for hepatic cells using coating/conjugation with Lactobionic acid, glycyrrhizin, and/or Galactosylated, in accordance with embodiments of the present invention.

FIG. 10 depicts A sketch illustrating the Design of cross-linked Chitosan nanoparticles for drug delivery—Nanoformulation are synthesized for the encapsulation of polymerase and protease inhibitors with or without interferon, with anti-fibrotic/anti-hemolytic agents' combination of naturally driven Polyphenol/Thiols, and Non-anticoagulant GAGs, and along with targeting for hepatic cells using coating/conjugation with Lactobionic acid, glycyrrhizin, and/or Galactosylated, in accordance with embodiments of the present invention.

Figure 11:
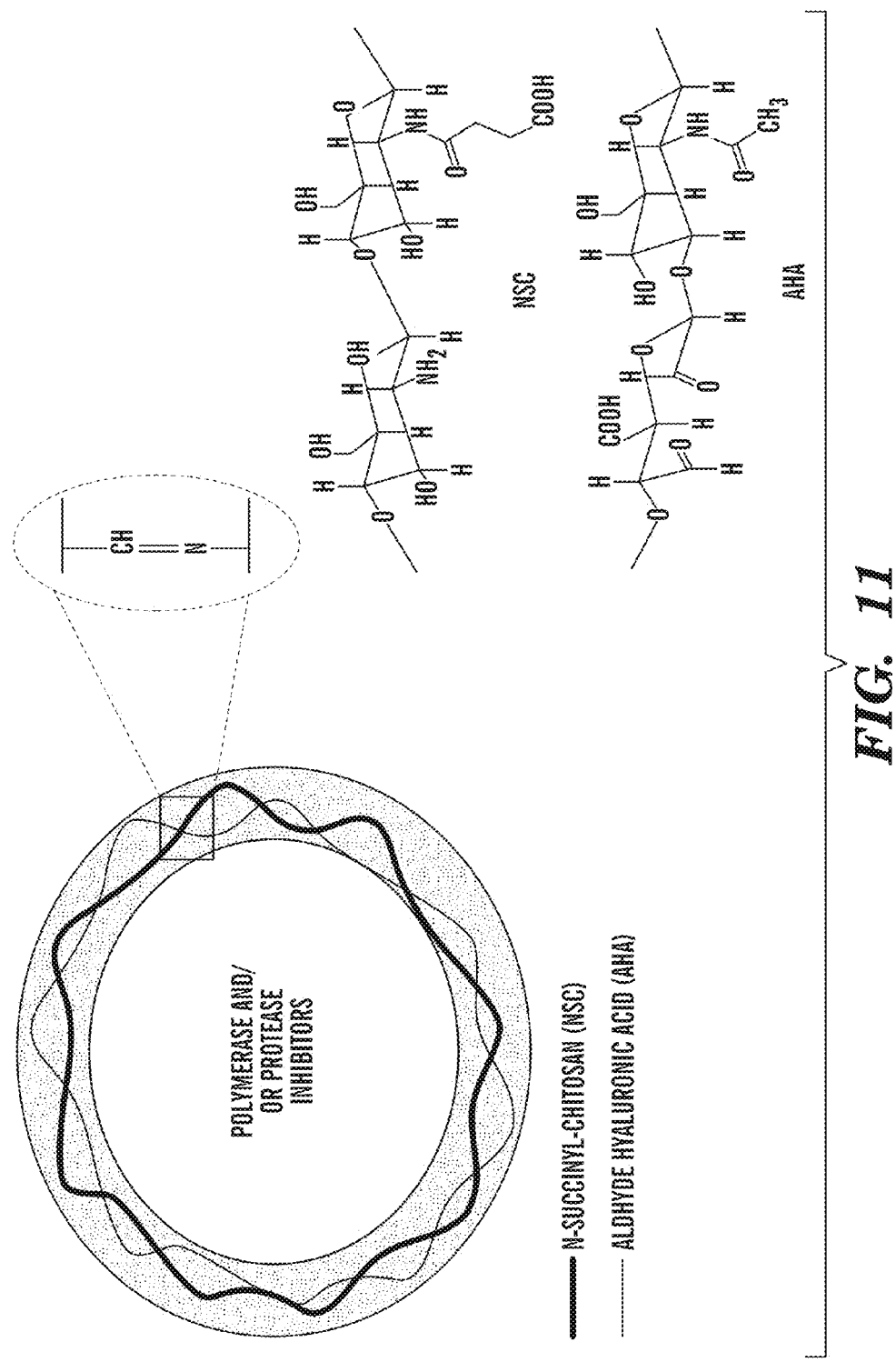
FIG. 11 depicts A sketch illustrating the Design of Hyaluronic acid (HA) cross-linked with Chitosan nanoparticles for drug delivery—Nanoformulation are synthesized for the encapsulation of polymerase and protease inhibitors with or without interferon, containing anti-fibrotic/anti-hemolytic agents, and along with targeting for hepatic cells using coating/conjugation with Lactobionic acid, glycyrrhizin, and/or Galactosylated, in accordance with embodiments of the present invention.

FIG. 11 depicts A sketch illustrating the Design of Hyaluronic acid (HA) cross-linked with Chitosan nanoparticles for drug delivery—Nanoformulation are synthesized for the encapsulation of polymerase and protease inhibitors with or without interferon, with anti-fibrotic/anti-hemolytic agents' combination of naturally driven Polyphenol/Thiols, and Non-anticoagulant GAGs, and along with targeting for hepatic cells using coating/conjugation with Lactobionic acid, glycyrrhizin, and/or Galactosylated, in accordance with embodiments of the present invention.

Figure 12:
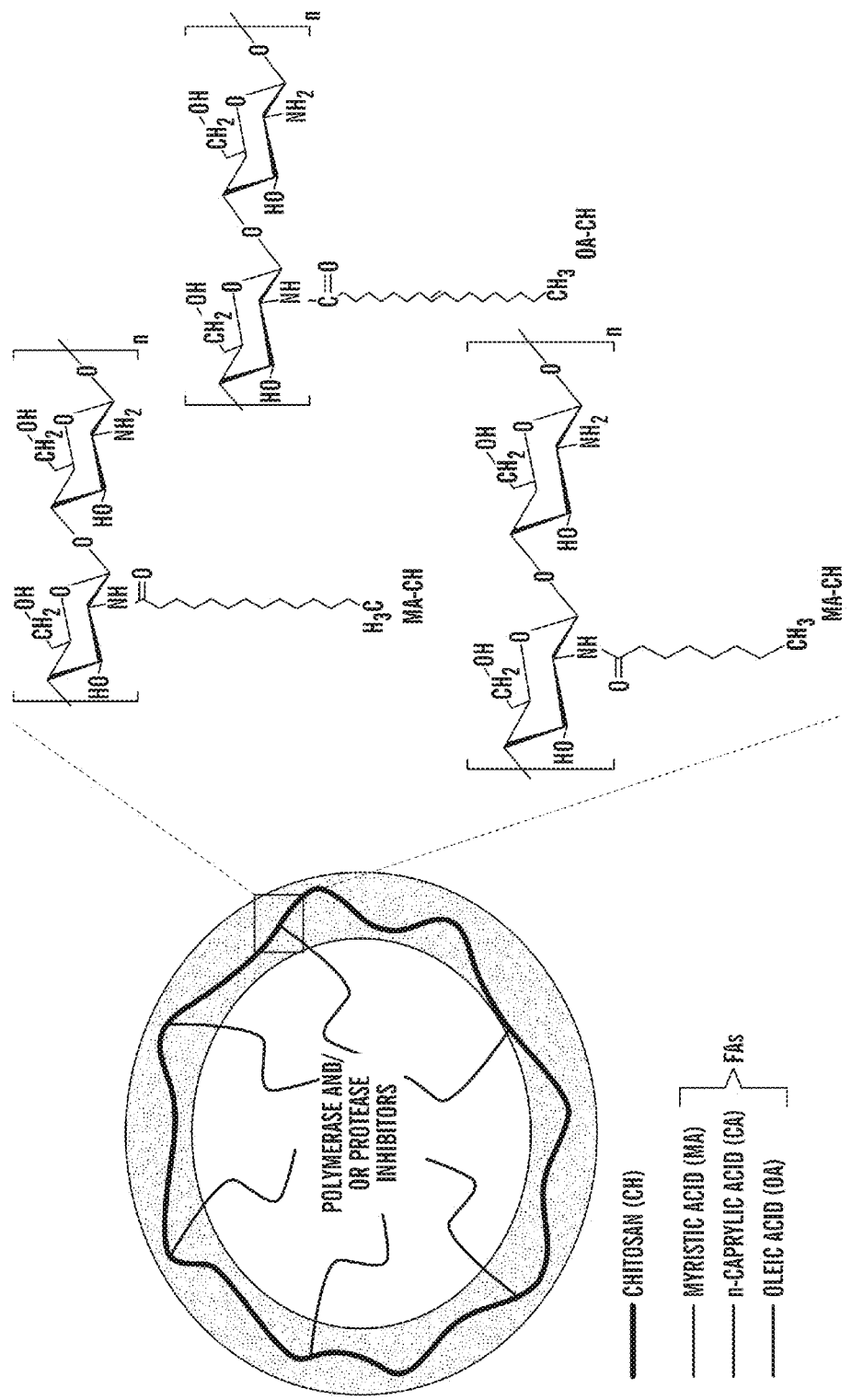
FIG. 12 depicts A sketch illustrating the Design of fatty acids (FA) cross-linked with Chitosan nanoparticles for drug delivery—Nanoformulation are synthesized for the encapsulation of polymerase and protease inhibitors with or without interferon, containing anti-fibrotic/anti-hemolytic agents, and along with targeting for hepatic cells using coating/conjugation with Lactobionic acid, glycyrrhizin, and/or Galactosylated, in accordance with embodiments of the present invention.

FIG. 12 depicts A sketch illustrating the Design of fatty acids (FA) cross-linked with Chitosan nanoparticles for drug delivery—Nanoformulation are synthesized for the encapsulation of polymerase and protease inhibitors with or without interferon, with anti-fibrotic/anti-hemolytic agents' combination of naturally driven Polyphenol/Thiols, and Non-anticoagulant GAGs, and along with targeting for hepatic cells using coating/conjugation with Lactobionic acid, glycyrrhizin, and/or Galactosylated, in accordance with embodiments of the present invention.

Figure 13:
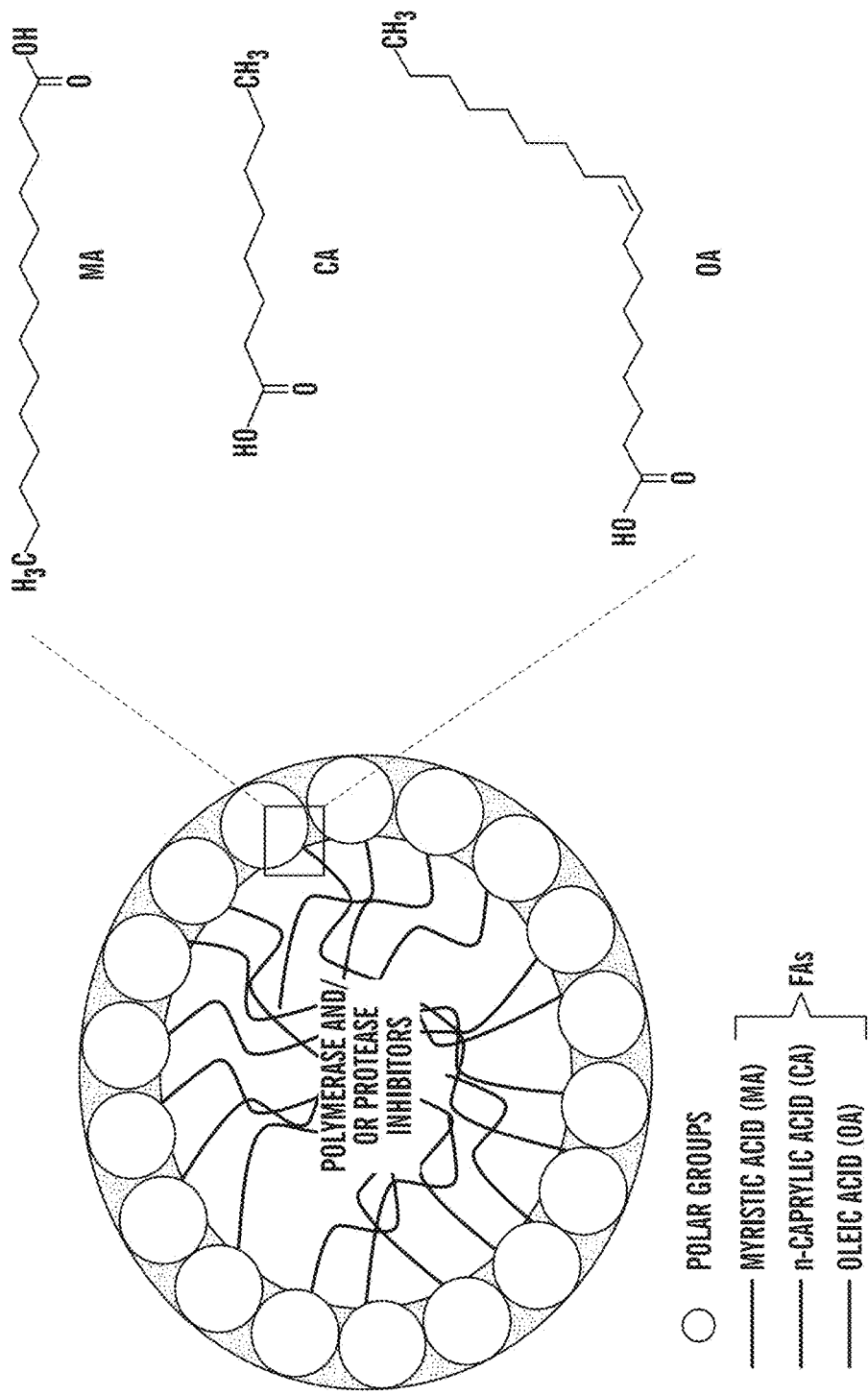
FIG. 13 depicts A sketch illustrating the Design of fatty acids (FA) nanoparticles for drug delivery—Nanoformulation are synthesized for the encapsulation of polymerase and protease inhibitors with or without interferon, containing anti-fibrotic/anti-hemolytic agents, and along with targeting for hepatic cells using coating/conjugation with Lactobionic acid, glycyrrhizin, and/or Galactosylated, in accordance with embodiments of the present invention.

FIG. 13 depicts A sketch illustrating the Design of fatty acids (FA) nanoparticles for drug delivery—Nanoformulation are synthesized for the encapsulation of polymerase and protease inhibitors with or without interferon, with anti-fibrotic/anti-hemolytic agents' combination of naturally driven Polyphenol/Thiols, and Non-anticoagulant GAGs, and along with targeting for hepatic cells using coating/conjugation with Lactobionic acid, glycyrrhizin, and/or Galactosylated, in accordance with embodiments of the present invention.

Figure 14:
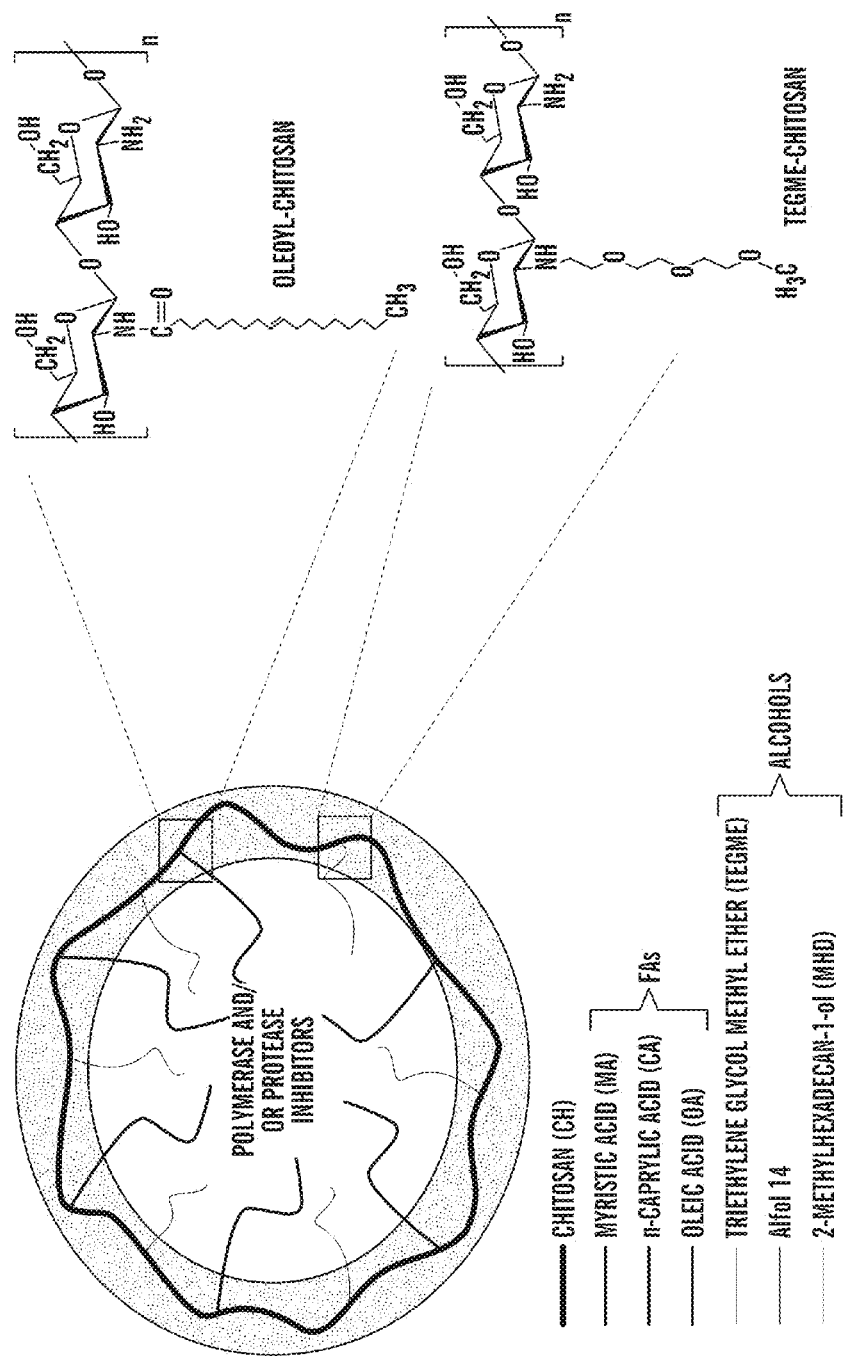
FIG. 14 depicts A sketch illustrating the Design of fatty acids (FA) cross linked to polyvinyl alcohol nanoparticles for drug delivery—Nanoformulation are synthesized for the encapsulation of polymerase and protease inhibitors with or without interferon, containing anti-fibrotic/anti-hemolytic agents, and along with targeting for hepatic cells using coating/conjugation with Lactobionic acid, glycyrrhizin, and/or Galactosylated, in accordance with embodiments of the present invention.

FIG. 14 depicts A sketch illustrating the Design of fatty acids (FA) cross linked to alcohol nanoparticles for drug delivery—Nanoformulation are synthesized for the encapsulation of polymerase and protease inhibitors with or without interferon, with anti-fibrotic/anti-hemolytic agents' combination of naturally driven Polyphenol/Thiols, and Non-anticoagulant GAGs, and along with targeting for hepatic cells using coating/conjugation with Lactobionic acid, glycyrrhizin, and/or Galactosylated, in accordance with embodiments of the present invention.

Figure 15:
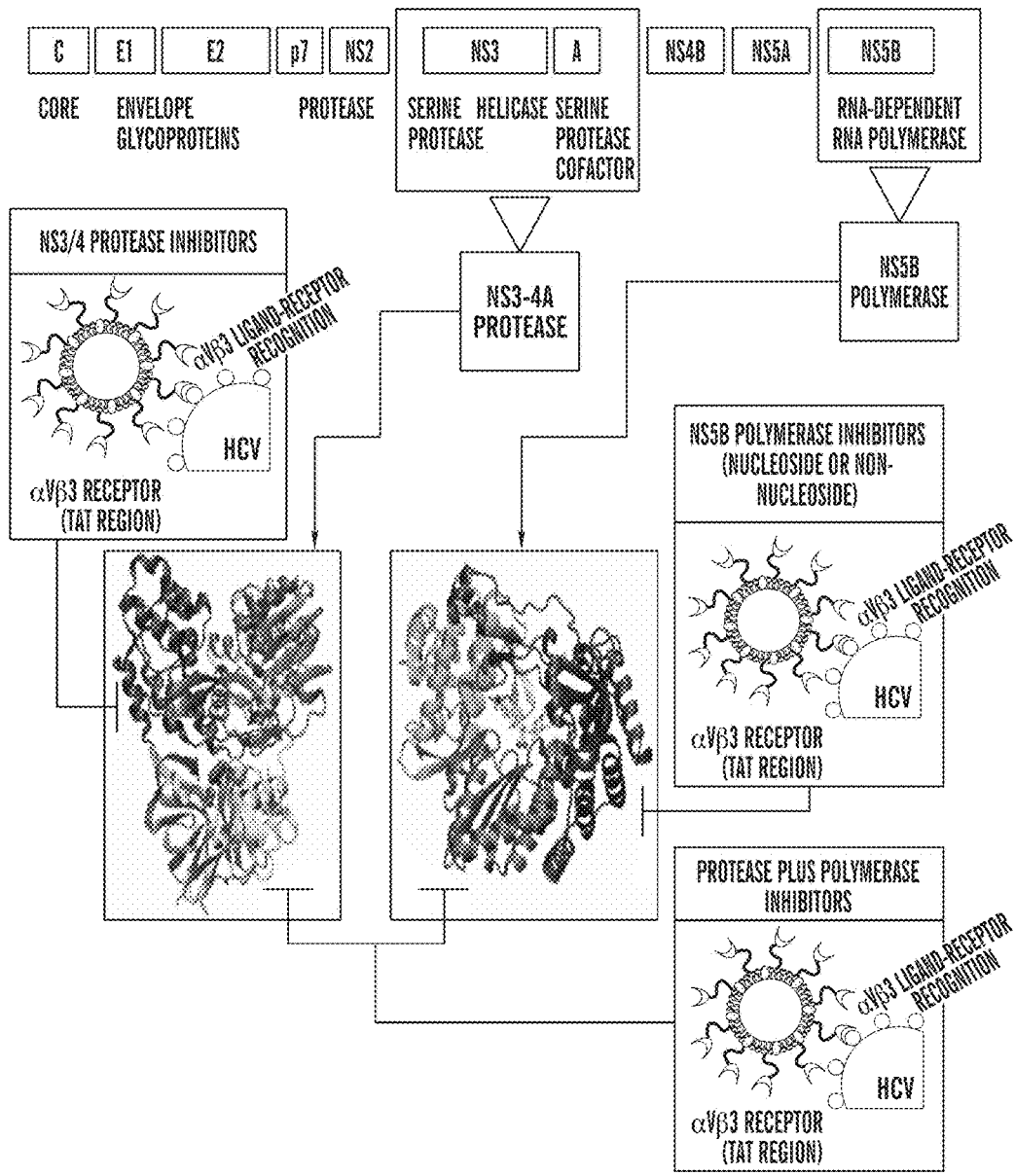
FIG. 15 depicts Illustrate the various anti-viral compounds that could be encapsulated for hepatic and/or viral targeting, in accordance with embodiments of the present invention.

FIG. 15 depicts Illustrate the various anti-viral compounds that could be encapsulated for hepatic and/or viral targeting, in accordance with embodiments of the present invention.

Example 1

Qualitative In Vitro Anti-HCV Screening

1—Detection of the Effect of the Prepared Compounds on Cancer Cell Line:

HepG2 cells were washed twice in RPMI1640 (Cambrex) media supplemented with 2000 µM L-glutamine (Cambrex) and 2504 HEPES buffer; N-[2-hydroxyethyl]piperazine-N'-[2-ethanesulphonic acid] (Cambrex) and were suspended at $2 \times 10^5$ cells $ml^{-1}$ in RPMI culture media (RPMI supplemented media, 10% fetal bovine serum (FBS); GIBCO-BRL). The cells were left to adhere on the polystyrene 6-well plates for 24 hours in 37° C., 5% $CO_2$, 95% humidity incubator. After 24 hr. the cells were washed twice from debris and dead cells by using RPMI supplemented media. Different concentrations (100, 50, 20, 10 or 5 µg/ml) from each prepared compound were added in 6-well plates. Positive and negative control cultures were included. Cultures were incubated for 72 hours in 37° C., 5% $CO_2$, 95% humidity. For examining the cell cycle of control and treated cells, the adherent cells were detached from the plate using 1 ml trypsin EDTA (200 mg/L for EDTA, 500 mg/L for trypsin in a ratio 1:250) for 1-3 minutes, the action of trypsin is stopped by the addition of 5 ml RPMI culture media. The cells were scrapped and collected in 15 ml falcon tube, then washed twice by RPMI supplemented media and once by phosphate buffer saline (PBS), after each wash centrifuge at 1000 rpm for 5 minutes. Resuspended the pellet in 1 ml Propidium iodide (Sigma) with concentration (50 ml/l in 0.1% sodium citrate and 01% triton X100), incubate the tubes in dark at 4° C. for at least 60 min. The effect of the compounds on HepG2 cell line was examined using FACS Calibur flow cytometer (BD Bioscience, San Diego, Calif., USA). The data were analyzed using MODFit (BD Bioscience).

Example 2

Qualitative in Vitro anti-HCV screening: Prepared compounds in the present study were investigated for its In Vitro action as anti-HCV using the hepatocellular carcinoma HepG2 cell line infected with the hepatitis-C virus. During the last few years, a number of cell culture systems showed to have the ability to harbor and support reliable and efficient progression of this virus. Among several human hepatocyte cell lines analyzed, the hepatocellular carcinoma HepG2 cell line was found to be most susceptible to the HCV infection. On the other hand, monitoring of the HCV viremia pre- and post-antiviral therapy through the detection of viral (+) and/or (−) RNA strands by the use of qualitative reverse transcription-polymerase chain reaction (RT-PCR) has become the most frequently-used, reliable and sensitive technique. Recently, it has been reported that the detection of the (−) strand HCV-RNA using the RT-PCR is a very important tool for understanding the life cycle of the HCV and provides a reliable marker for the diagnosis of HCV and monitoring the viral response to antiviral therapy.

Based on these facts, the adopted method in the present study contributes to the simultaneous detection of the (+) and/or (−) HCV-RNA strands in HepG2 hepatoma cells infected with HCV. Inhibition of viral replication were detected by amplification of viral RNA segments using the RT-PCR technique, both in the cultivated cells alone (as a positive control) and in the presence of variable concentrations of the test compounds at optimal temperature. The test compound is considered to be active when it is capable of inhibiting the viral replication inside the HCV-infected HepG2 cells, as evidenced by the disappearance of the (+) and/or (−) strands viral RNA-amplified products detected by the RT-PCR (compared with the positive control).

Using the same method HCV replication were examined in peripheral blood cells from 10-20 HCV infected patients before and after subjected their cells in an In Vitro culture to different concentrations of the prepared compounds in the present proposal.

Example 3

Flow cytometry analysis of intracellular staining of HCV core antigen in infected HepG2 cells: The intracellular staining of HCV core antigen in HCV infected HepG2 cells were quantified before and after incubation with the different concentrations of the test compounds by using a fluorescence activated cell sorting (FACS) based assay. Intracellular staining labeling was performed by direct immunofluorescence. HepG2 cells (collected after addition of trypsin) were centrifuged and supernatants were removed. Cell pellets were washed 4 times with PBS. For intracellular staining, cells were incubated with 4% paraformaldehyde for 10 min and 0.1% Triton X-100 in Tris buffer (pH 7.4) for 6 min. After washed with PBS, cells were incubated with FITC-labeled F (ab)2 portion of HCV core antibody (at 1:2000 dilutions or according to previous standardization) for 30 min at 4° C. Cells were washed with PBS containing 1% normal goat serum and suspended in 500 µl and were analyzed by flow cytometry (FACS Calibure, BD). Mean fluorescence intensity were determined using Cell Quest software (Becton Dickinson)

Example 4

Synthesis of Chitosan Grafted Poly(Lactic-Co-Glycolic Acid) (PLGA) Nanoparticles Synthesis of chitosan grafted PLGA nanoparticles using a modification a double emulsion-diffusion-evaporation technique described by Kumar et al (25). Thus, with slight modification of this method we have already demonstrated our ability to synthesis chitosan grafted PLGA nanoparticles. Thus, using emulsion technique we can synthesis nanoparticles of size of around ~250 nm in diameter. The size of the nanoparticles is determined using dynamic light scattering (DLS) (FIG. 1).

Example 5

Cellular Uptake of Chitosan Grafted PLGA Nanoparticles

Cell Culture: HepG2 cells grown in Eagle's Minimum Essential Medium (EMEM) (Invitrogen, Grand Island, N.Y.) supplemented with 10% fetal calf serum (Atlanta Biologicals, Lawrenceville, Ga., USA). Penicillin/streptomycin (1%) was also present in the culture media (Invitrogen, Grand Island, N.Y., USA). The cells were trypsinized, subjected to centrifugation, and then the cell pellet was resuspended in suitable media. An aliquot (1 mL) of the suspension was transferred to a 35-mm glass bottom culture dishes (MatTek Corp., Ashlan, Mass., USA), and the cells incubated for 24 hours (hrs) at 37° C. under a 5% $CO_2$ atmosphere (Thermo Electron Corp., Forma Series II).

Figure 2:
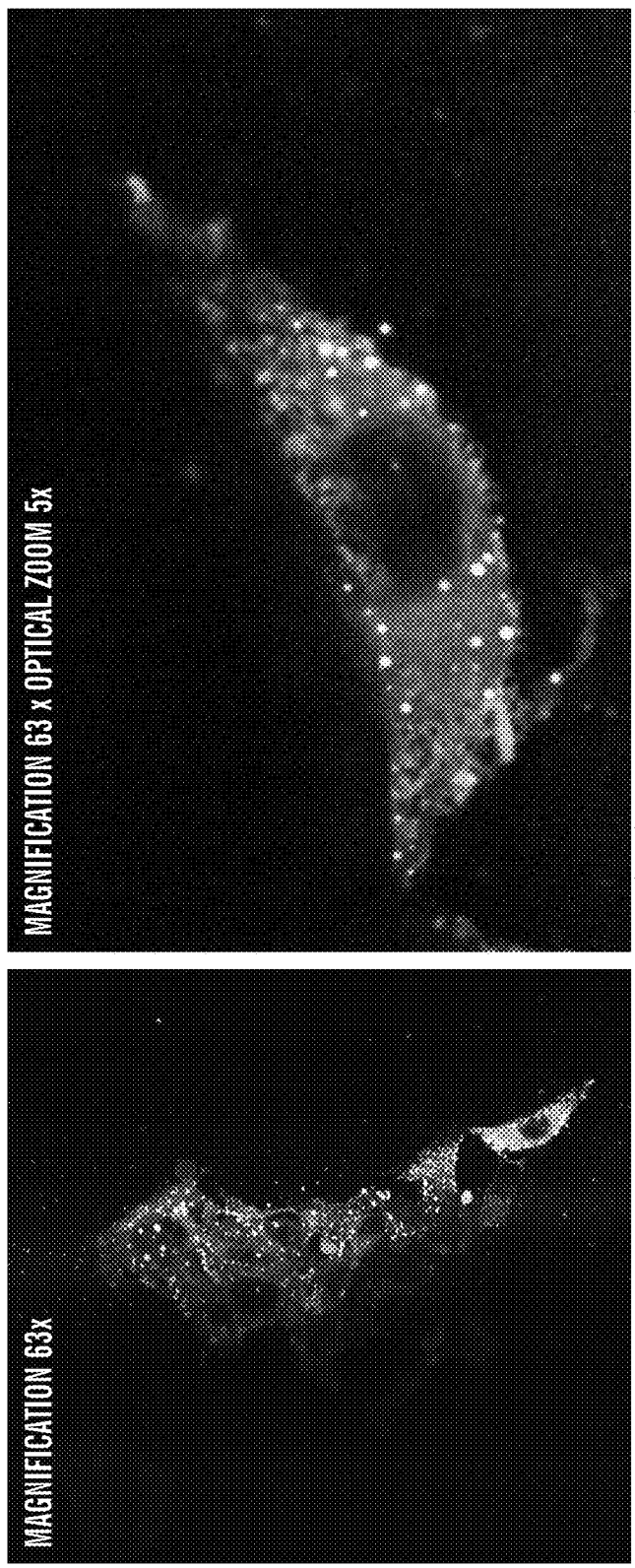
FIG. 2 depicts Confocal imaging of HepG2 cell showing the uptake of Cy3-labeled chitosan grafted PLGA nanoparticles, in accordance with embodiments of the present invention.

Confocal Imaging: HepG 2 cells cultured as described above and treated with Cy3 dye-labeled chitosan grafted PLGA nanoparticles (37° C., 5% $CO_2$) for 2 hrs. After 2 hrs, cells were washed several time with phosphate buffered saline (PBS), and then fixed in 1% formaldehyde (Sigma, St. Louis Mo., USA). Confocal images were taken using a Leica TCS SP5 confocal microscope equipped with a 63×(NA=1.3 glycerol immersion) objective, a 543 nm excitation wavelength and an emission filter for detection between 555 nm and 620 nm (FIG. 2).

Example 6

We synthesized three different polymeric nano-formulations, as listed below. The invention combines known polymerase inhibitor such as (Compound A) Isopropyl (2S)-2-[(2R,3R, 4R, 5R)-5-(2,4-dioxopyrimidin-1-yl)-4-fluoro-3-hydroxy-4-methyl-tetrahydrofuran-2-yl]methoxy-phenoxy-phosphoryl]amino]propionate with known protease inhibitor such as (Compound B) 1-[(2R,3R,4S,5R)-3,4-dihydroxy-5-(hydroxymethyl)oxolan-2-yl]-1H-1,2,4-triazole-3-carbox amide at 500 mg and 1000 mg were co-encapsulated in the nanoparticles along with IFNγ, with anti-fibrotic/anti-hemolytic agents' combination of naturally driven Polyphenol/Thiols, and Non-anticoagulant GAGs.
  1. cross-linked polyvinyl pyrrolidone (PVP) hydrogel nanoparticles
  2. alginate-chitosan nanoparticles
  3. chitosan grafted poly(lactic-co-glycolic acid) (PLGA) nanoparticles The nanoparticles were synthesized and characterized using dynamic light scattering (DLS) and transmission electron microscopy (TEM). Uptake of the nanoparticles was examined in the human hepatocellular HepG2 cell line using confocal microscopy. Based on in vitro release kinetics, entrapment efficiency and in vitro uptake in HepG2 cells, the three most effective formulations were chosen for further studies.

Example 7

Synthesis of Alginate-Chitosan Nanoparticles

Alginate-chitosan nanoparticles encapsulating IFN γ were synthesized using the ionic gelation method (33-34). Low viscosity sodium alginate and low molecular weight chitosan were used for the synthesis of the nanoparticles. The alginate solution was prepared in deionized water; the chitosan solution was prepared in 1% v/v acetic acid. The pH of both solutions were adjusted to approximately 6.0, and the solutions were filtered (0.22 μm pore size) prior to use. Nanoparticles were prepared under sterile conditions by mixing appropriate volumes of 0.005% (w/w) sodium alginate and IFN followed by the addition of 1% (w/w) chitosan under stirring for 2 hours (hrs) at room temperature. The amount of IFN was adjusted until we achieve maximum loading efficiency. Nanoparticles were characterized by DLS, zeta size and TEM. For co-encapsulation of Sofosbuvir, ribavirin with or without IFN γ, an appropriate amount of Sofosbuvir and ribavirin were added to the solution along with IFN γ.

Example 8

Synthesis of hybrid cross-linked PVP hydrogel nanoparticles: Nanoparticles encapsulating IFN were synthesized by in situ polymerization of various monomers, as described below. Polymerization reactions were carried in a reverse micelle environment. Sodium bisethylhexylsulphosuccinate or aerosol OT (AOT; Sigma Aldrich, St. Louis, Mo., USA) were used as a surfactant for micelle formation. Surfactant (either sodium bisethylhexylsulphosuccinate or AOT) were dissolved in n-hexane (typically 0.03M to 0.1M AOT in hexane). Aqueous solutions of monomer were added together with the cross-linking reagent N N' methylenebisacrylamide (MBA), the initiator ammonium persulphate (APS), the activator ferrous ammonium sulphate (FAS), and where indicated, an aqueous solution of IFN. The polymerization reaction was carried out in the presence of $N_2$ gas. The monomers to be tested are vinylpyrrolidone (VP), N-isopropylacrylamide (NIPAAM) and N-3 aminopropylmethylacrylamide (APAAM). For co-encapsulation, taribavirin were added along with IFN to the reverse micelles. To initiate the polymerization reaction, we were use 15 μl of a saturated solution of APS (2% w/w of monomers) and 20 μl of a 0.05% w/v solution FAS (0.07% w/w of monomers). The reaction was allowed to proceed at room temperature for 2-3 hrs.

Example 9

Synthesis of Chitosan Grafted PLGA Nanoparticles

Chitosan grafted PLGA nanoparticles were prepared by a modification of a method originally described by Kumar et al (25). In brief, this double emulsion-diffusion-evaporation technique of synthesis of nanoparticles is as follows: 50 mg of PLGA were dissolved in 2 mL of ethyl acetate, and then 200 ul of a solution of IFN were added. The mixture were sonicated for 5 seconds using a probe sonicator, and then the emulsion were immediately be added to an aqueous stabilizer mixture, containing 100 mg of polyvinyl alcohol (PVA) and 10 mg of chitosan in 10 ml of water, drop wise with stirring. The entire solution was sonicated again for approximately 10 seconds using a probe sonicator. The emulsion was stirred at room temperature for 1 hr, and then the organic phase was removed using a rotatory evaporator. For co-encapsulation of taribavirin, an appropriate amount of taribavirin was added along with IFNγ during the synthesis step.

Example 10

Entrapment Efficiency

Entrapment efficiency for IFNγ and taribavirin were determined by filtering a known amount of the nanoparticles through a 0.1 μm filter membrane to separate free IFN and taribavirin. The amount of active IFN was determined using the Bioplex system, available at PRI; the amount of taribavirin was determined using high performance liquid chromatography (HPLC). Entrapment efficiency (E %) were determined based on the total concentration of drug (IFNγ or taribavirin) in the system (free+encapsulated; $[Drug]_0$) and the concentration of drug in the filtrate ($[Drug]_f$) using the following formula:

$$E\ \% = (([Drug]_0 - [Drug]_f)/[Drug]_0) \times 100$$

Example 11

Release Kinetics of IFNγ, Ribavirin or Taribavirin and Sovosbuvir from the Nanoparticles The in vitro release kinetics of the nanoparticles were evaluated in phosphate buffered saline (PBS) and fetal bovine serum (FBS). A defined amount of IFN and taribavirin encapsulated in nanoparticles were suspended in 10 ml of PBS, and the solution was kept at room temperature. At various time intervals, the solution were vortexed, and an aliquot (1 mL) of the solution removed and subjected to centrifugation at 13,000 rpm to separate released drug (IFNγ/taribavirin or ribavirin) from nanoparticle-encapsulated material. The concentration of released drug was determined by Bioplex assay (for IFNγ) and HPLC (for taribavirin). The percent release of IFNγ/ribavirin was determined according to the following formula:

$$\%\ Release = ([Drug]_{f,t} / [Drug]_0) \times 100$$

Where $[Drug]_{f,t}$ is the concentration of IFNγ or taribavirin in the supernatant at time t. Similarly, to determine the release kinetics in FBS, a defined amount of IFNγ taribavirin encapsulated in nanoparticles were suspended in 10 ml of 20% FBS. Release kinetics was analyzed as described for PBS.

Example 12

Analysis of Particle Size by DLS and TEM

Size distribution of IFN and taribavirin-encapsulated nanoparticles in an aqueous dispersion were determined using a Malvern zeta sizer (Malvern Instrumentation Co, Westborough, Mass., USA). The size and morphology of the nanoparticles were also examined using a JEOL JEM-100CX transmission electron microscope.

Example 13

Conjugation of Monoclonal Antibody/TAT Peptide/p14 Peptide (NS3 Peptide)

Figure 3:
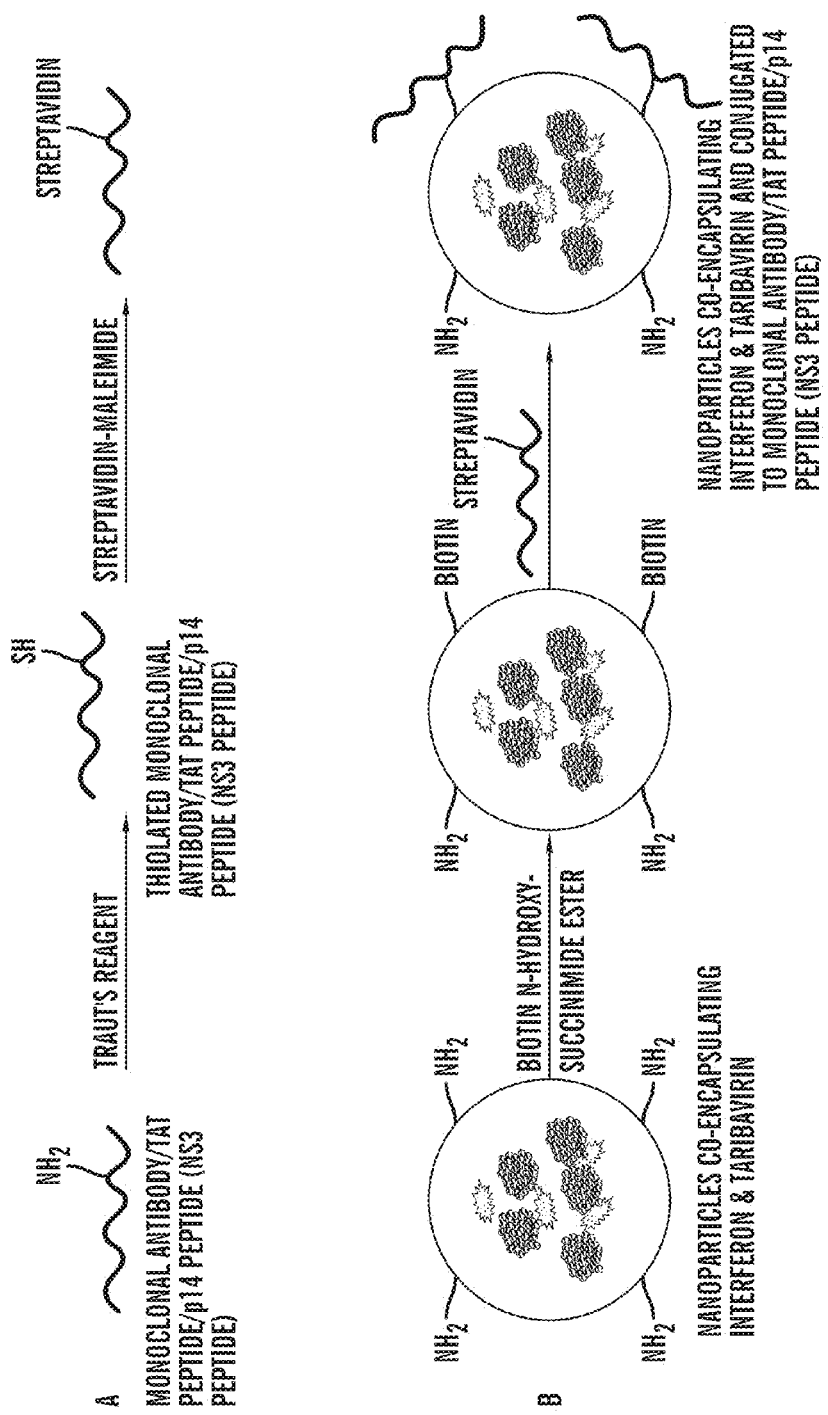
FIG. 3 depicts Schematic diagram showing conjugation strategy for linking monoclonal antibody/TAT Peptide/p14 peptide (NS3 peptide) nanoparticles, in accordance with embodiments of the present invention.
Figure 4:
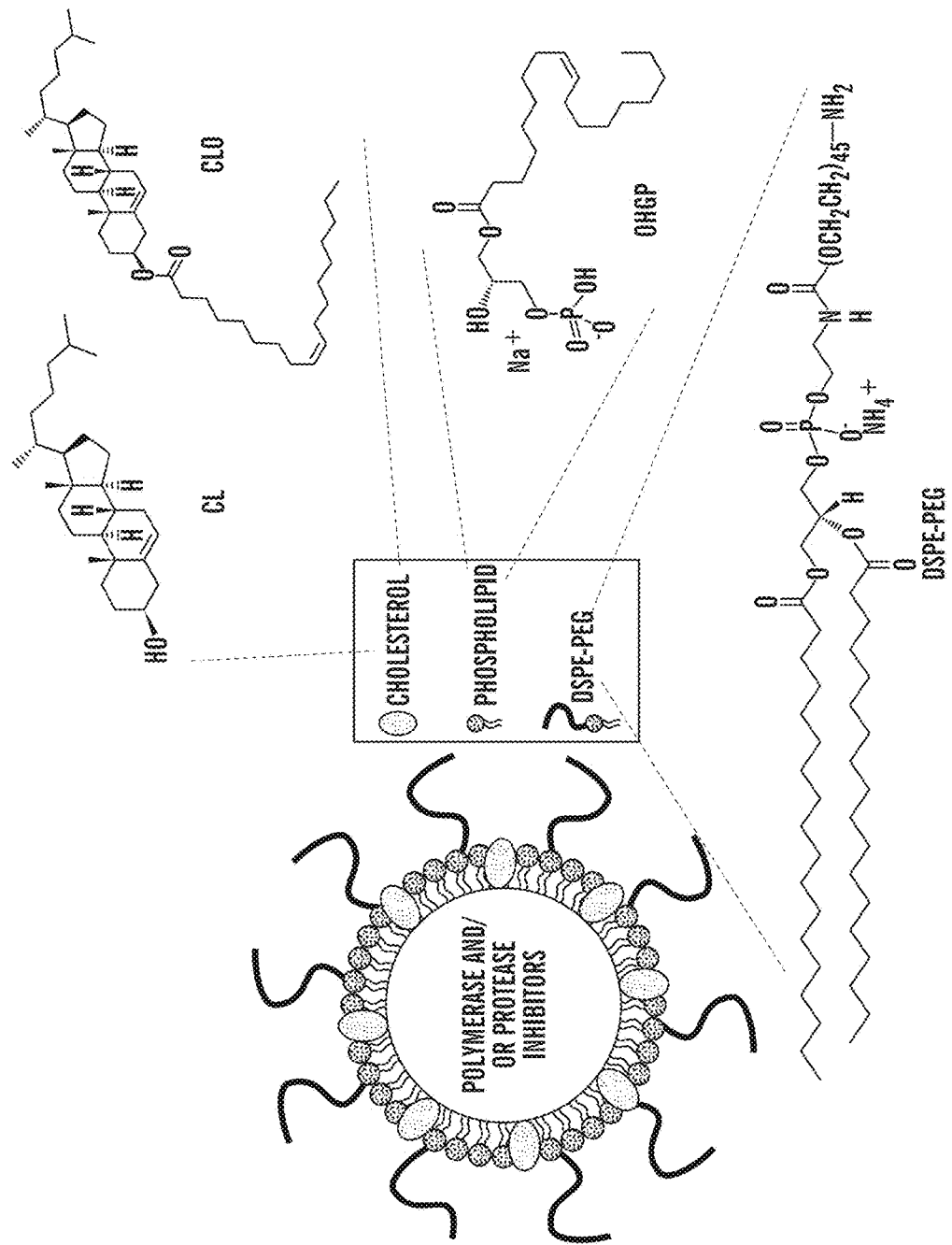
FIG. 4 depicts A sketch illustrating the Design of Solid lipid nanoparticles (SLN) for drug delivery—Nanoformulation are synthesized for the encapsulation of polymerase and protease inhibitors with or without interferon, containing anti-fibrotic/anti-hemolytic agents, and along with targeting for hepatic cells using Lactobionic acid, glycyrrhizin, and/or Galactosylated, in accordance with embodiments of the present invention.
Figure 5:
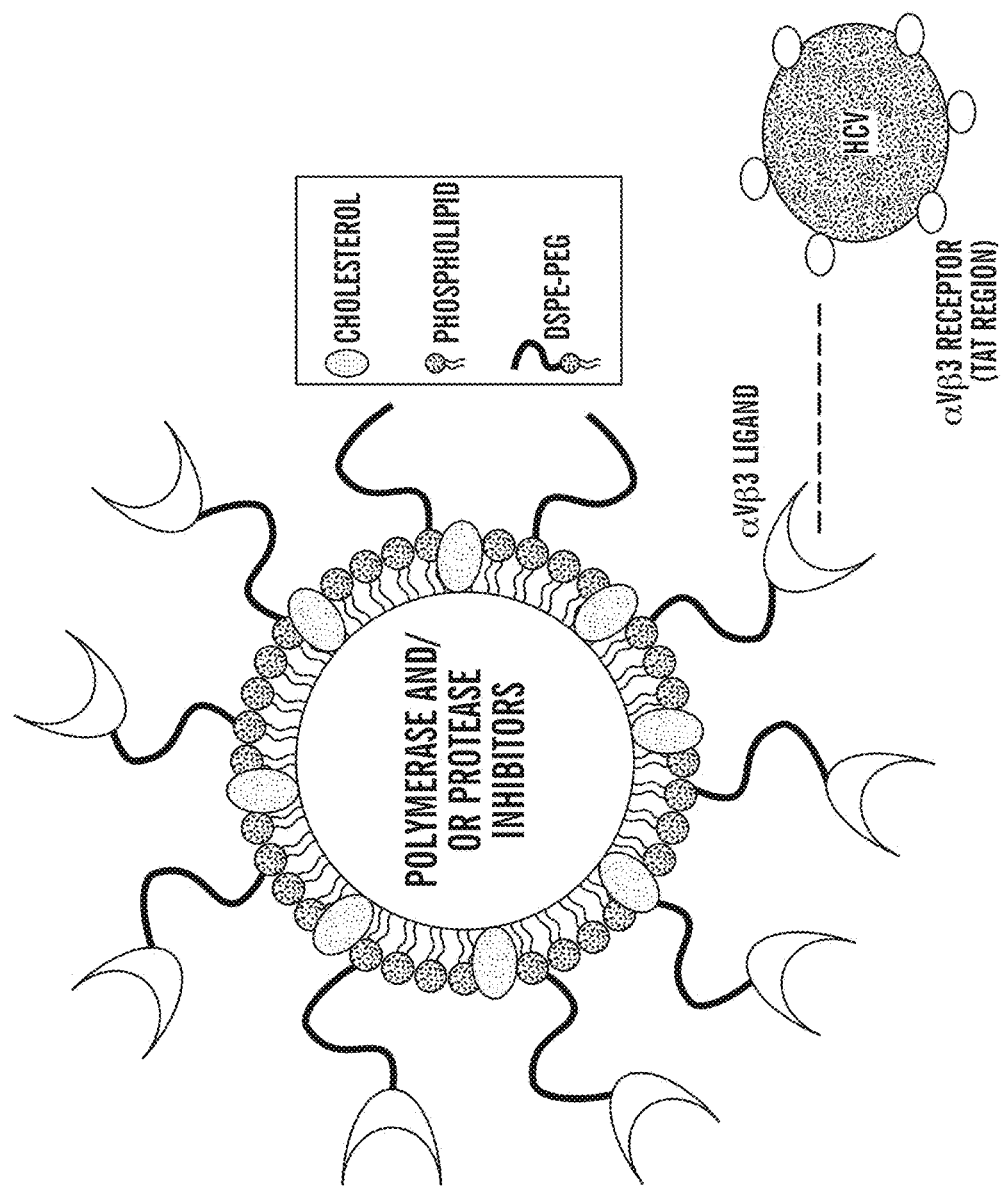
FIG. 5 depicts A sketch illustrating the Design of Solid lipid nanoparticles (SLN) for drug delivery—Nanoformulation are synthesized for the encapsulation of polymerase and protease inhibitors with or without interferon, containing anti-fibrotic/anti-hemolytic agents, and along with targeting for hepatitis C virus can be targeted by conjugation of high affinity αvβ3 ligand and coating/conjugation for hepatic cells using Lactobionic acid, glycyrrhizin, and/or Galactosylated, in accordance with embodiments of the present invention.
Figure 6:
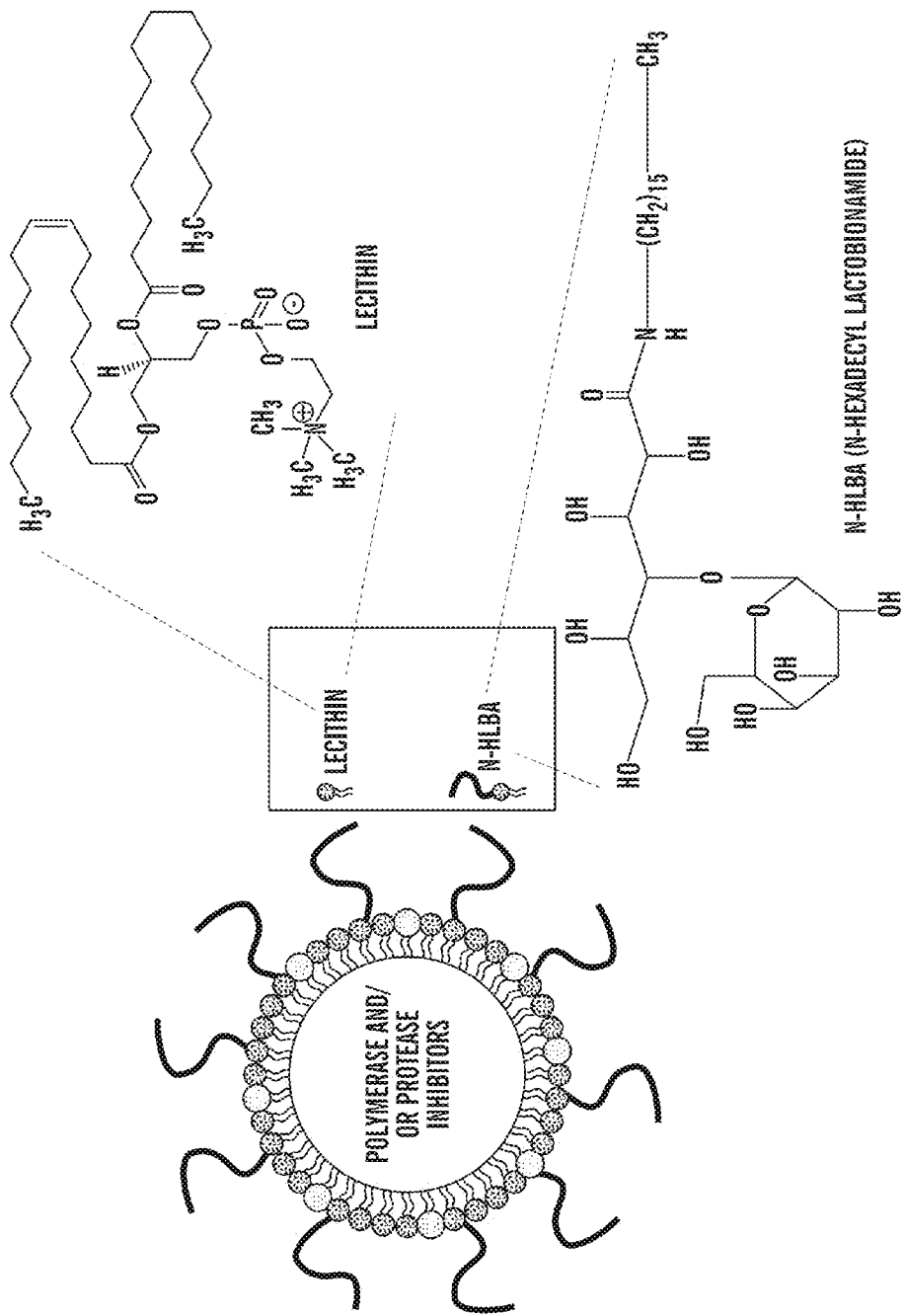
FIG. 6 depicts A sketch illustrating the Design of nanoparticles for drug delivery—Nanoformulation are synthesized for the encapsulation of polymerase and protease inhibitors with or without interferon, containing anti-fibrotic/anti-hemolytic agents, and along with targeting for hepatic cells using coating/conjugation with Lactobionic acid, glycyrrhizin, and/or Galactosylated, in accordance with embodiments of the present invention.

A schematic diagram of the nanoparticle conjugation scheme is shown in FIG. 3. Surface functionalization and different conjugation chemistries were used to obtain nanoformulations co-encapsulating IFN and taribavirin, monoclonal antibody/TAT Peptide/p14 peptide (NS3 peptide). Nanoparticles were conjugated monoclonal antibody/TAT Peptide/p14 peptide (NS3 peptide) using streptavidin/biotin chemistry. The three types of nanoparticles described above contain free amino groups on their surface. Thus, amino-functionalized nanoparticles can be readily biotinylated using the appropriate amount of N-hydroxysuccinimidobiotin (Sigma-Aldrich, Saint Louis, Mo., USA). monoclonal antibody/TAT Peptide/p14 peptide (NS3 peptide) were first thiolated in side-by-side reactions using Traut's reagent (Pierce Biotechnology, Inc., Rockford, Ill., USA) (35-37), followed by the addition of streptavidin-maleimide (Sigma-Aldrich) to generate streptavidin-conjugated monoclonal antibody/TAT Peptide/p14 peptide (NS3 peptide) (FIG. 3). Thus, nanoparticles can be further subdivide into three different categories from each above mentioned type of nanoparticles (based on the targeted moiety): All the nanoformulations were have co-encapsulating IFN and taribavirin and A) Nanoformulation 1: conjugated to monoclonal antibody; B) Nanoformulation 2: conjugated to TAT Peptide and) Nanoformulation 3: conjugated to p14 peptide (NS3 peptide).

Example 14

In Vitro Efficacy Test

In vitro uptake were determined by confocal microscopy using dye-labeled nanoparticles. The human hepatocellular liver carcinoma cell line HepG2 was used, and all of the nanoparticle formulations described above were conjugated to Alexa Fluor 488. All of the nanoparticles contain a sufficient amount of free amino groups on their surface; thus, we were use the commercially available (Invitrogen Corp, Carlsbad, Calif., USA) Alexa Fluor 488 N-hydroxysuccinimide ester for conjugating the dye to the nanoparticles, according to the manufacturer's instructions.

Example 15

Cell Culture: HepG2 cells were grown in Eagle's Minimum Essential Medium (EMEM) (Invitrogen, Grand Island, N.Y., USA) supplemented with 10% fetal calf serum (Atlanta Biologicals, Lawrenceville, Ga., USA). Penicillin/streptomycin (1%) was also present in the culture media (Invitrogen). The cells were trypsinized and collected by centrifugation, and then the cell pellet was resuspended in suitable media. An aliquot (1 mL) of the cell suspension were transferred to 35-mm glass-bottom culture dishes (MatTek Corp., Ashlan, Mass., USA) and the cells were allowed to incubate for 24 hrs at 37° C. in a 5% $CO_2$ atmosphere (Thermo Electron Corp., Forma Series II).

Example 16

Confocal Imaging: HepG2 cells were incubated with dye-labeled nanoparticles at 37° C., 5% $CO_2$ for pre-determined periods of time. After each specific time interval (1, 2, 4, and 6 hrs.), the plates were washed several times with PBS and then the cells were fixed in 1% formaldehyde (Sigma-Aldrich). Confocal images were taken using a Leica TCS SP5 confocal microscope equipped with a 63× objective (NA=1.3 glycerol immersion). Excitation was at 405 nm and was detected between 508 nm and 530 nm. Based on the results obtained from size measurement, release kinetics, entrapment efficiency and confocal imaging, 2 nanoformulations from each category (3×3=9) were selected for further studies.

Example 17

Cell Cycle Effect of the Prepared Compounds

HepG2 cells were washed twice in RPMI1640 (Cambrex) supplemented with 200 μM L-glutamine (Cambrex) and 2504 HEPES buffer (Cambrex), and then suspended at a density of $2\times10^5$ cells/ml in RPMI culture media (RPMI supplemented with 10% FBS (Gibco-BRL/Invitrogen, Carlsbad, Calif., USA). Cells were allowed to adhere to 6-well polystyrene plates for 24 hrs at 37° C. under 5% $CO_2$, 95% humidity. After 24 hrs. the cells were washed twice to remove debris and dead cells using RPMI supplemented media. Different concentrations (100, 50, 20, 10 or 5 μm/ml) of each prepared compound were added to the plates. Positive and negative control cultures were included. Cultures were incubated for 72 hrs at 37° C., 5% $CO_2$, 95% humidity. To determine the effect of the compounds on the cell cycle, adherent control and treated cells were detached from the plate using 1 mL of trypsin: EDTA (200 mg/L EDTA, 500 mg/L trypsin; 1:250) for 1-3 minutes, and then trypsin were inhibited by the addition of 5 mL of RPMI culture media. The cells were scraped and collected in a 15 ml falcon tube, then washed twice using RPMI supplemented media, followed by washing once in PBS. After each wash, cells were collected by centrifugation at 1000 rpm for 5 minutes. Cells were resuspended in 1 ml of propidium iodide (PI; Sigma) (50 ml/L in 0.1% sodium citrate, 01% triton X-100), and then incubated in the dark at 4° C. for at least 60 minutes. The cell cycle effect of the compounds on HepG2 cells were examined by FACS Calibur flow cytometry (BD Bioscience, San Diego, Calif., USA) and data were analyzed using MODFit (BD Bioscience).

Example 18

Qualitative In Vitro Anti-HCV Screening

Compounds were investigated for their activity in vitro as anti-HCV agents using HepG2 cells infected with HCV. Among several human hepatocyte cell lines analyzed, HepG2 cells found to be the most susceptible to HCV infection. Detection of positive (+) and/or negative (−) viral RNA strands by qualitative reverse transcription-polymerase chain reaction (RT-PCR) has become the most frequently-used, reliable and sensitive technique for monitoring HCV viremia pre- and post-antiviral therapy. Recently, it was shown that detection of (−) strand HCV mRNA using RT-PCR is a very important tool for understanding the life cycle of HCV, and provides a reliable marker for the diagnosis of HCV and for monitoring viral response to antiviral therapy. The method adopted for the current study allows for simultaneous detection of (+) and/or (−) strand HCV mRNA in HepG2 cells infected with HCV. Viral replication were detected by amplification of specific viral RNA segments using RT-PCR from cells cultivated alone (as a positive control) and in the presence of variable concentrations of test compound at optimal temperature. The test compound were considered active when it is capable of inhibiting viral replication in HCV-infected HepG2 cells, as evidenced by the disappearance of amplified (+) and/or (−) strand viral mRNA products (as compared to the positive control). Using the same method, HCV replication were examined in peripheral blood cells isolated from 10-20 HCV-infected patients before and after the cells are cultured in vitro in the presence of different concentrations of prepared compounds.

Example 19

Flow Cytometry Analysis of Intracellular HCV Core Antigen in Infected HepG2 Cells The presence of intracellular HCV core antigen in HCV infected HepG2 cells were quantified before and after incubation with different concentrations of test compounds using fluorescence activated cell sorting (FACS). Intracellular localization of HCV core antigen was carried out using direct immunofluorescence staining HepG2 cells (after trypsinization) were collected by centrifugation, and the supernatants were removed. Cell pellets were washed 4 times with PBS. For intracellular staining, cells were incubated in 4% paraformaldehyde for 10 minutes, followed by 0.1% Triton X-100 in Tris buffer (pH 7.4) for 6 minutes. After washing with PBS, cells were incubated with FITC-labeled anti-HCV core antibody (F (ab)2 portion; 1:2000 dilution, or as determined by prior standardization) for 30 minutes at 4° C. Cells were washed with PBS containing 1% normal goat serum, resuspended in 500 μL, and then analyzed by flow cytometry (FACS Calibur, BD). Mean fluorescence intensity were determined using Cell Quest software (Becton Dickinson).

Aim 3: The immunodeficient uPA mouse model were used to determine the in vivo efficacy of nanoformulations incorporating IFN and taribavarin The uPA/SCID mouse model is one of the models most closely related to human physiology, as the humanized liver contains as high as 75% human hepatocytes. Thus, this model has tremendous potential to serve as a bridge between the in vitro work and clinical research.

Example 20

Chimeric uPA-SCID mice engrafted with human hepatocytes were used to determine the in vivo efficacy of selected nanoformulations. The uPA-SCID mice engrafted with human hepatocytes were generated. Mice were maintained in a barrier facility in HEPA-filtered racks. The animals were fed a sterilized laboratory rodent diet.

Treatments: Mice that are infected with HCV were treated with the best from the nanoformulation chosen from each category of the nanoformulation 1, 2 or 3 or controls (see below), by intraperitoneal injection of the optimum dose every other day for 14 days. To determine anti-HCV efficacy, a pilot study was performed to determine the optimum dose needed in the mouse model. Blood samples were collected from the tail vein in every other day for 10 days after the conclusion of treatment. The animals were divided into the following experimental groups:

Treatment Groups
1. Control animals; untreated, n=10
2. Control animals; n=10, void nanoparticle (formulation 1)
3. Control animals; n=10, void nanoparticle (formulation 2)
4. Control animals; n=10, void nanoparticle (formulation 3)
5. Control animals; IFNγ alone
6. Control animals; n=10 ribavirin alone.
7. Control animals; n=10 Sofosbuvir alone
8. Test animals: n=10, nanoformulation 1
9. Test animals: n=10, nanoformulation 2
10. Test animals: n=10, nanoformulation 3

HCV viremia in the blood samples before and after administration of nanoformulations (or controls) were monitored by detection of (+) and/or (−) viral mRNA using RT-PCR.

Example 21

Statistical Analysis

Values were computed for individual animals and for groups of animals, and differences between groups were analyzed using the Student's t-test or Mann Whitney-U test based on the distribution of data. Mean values for each treatment group were derived by combining single experimental values for each animal within the group. ANOVA were used to test differences among several treatment group means. A P value <0.05 was considered statistically significant.

In vitro and in vivo studies identified 2′-Cmethylcytidine prodrugs of a polymerase inhibitor that could help treat HCV. In cell-based assays, the prodrugs inhibited HCV NS5B polymerase with 10- to 200-fold better potency than the parent compound. In hamsters and rats, subcutaneous administration of the prodrug led to accumulation of the active compound in the liver without the generation of toxic metabolites.

Example 22

Galactosylated Solid Lipid Nanoparticles: (SLN)

Preparations (I): 100 mg Lactobionic acid calcium salt/5 ml D.D.H₂O, 150 mg N-Hydroxysuccinimide (NHS), 150 mg N-(3-Dimethyl amino propyl)-N'-ethyl-carbodiimide hydrochloride, Mixing them together and stirring were done for 1 hr. and then 100 mg Hexadecylamine was added Preparations (II): 1.5 g Lecithin, 10 ml Pluronic F68, 5 ml Tween 80, Mix and complete them to 100 ml DD.H₂O, and Stirring for 72 hrs.

While particular embodiments of the present invention have been described herein for purposes of illustration, many modifications and changes will become apparent to those skilled in the art. Accordingly, the appended claims are intended to encompass all such modifications and changes as fall within the true spirit and scope of this invention.

What is claimed is:

1. A composition, comprising a Nanoformulation, said Nanoformulation comprising:
   a protease inhibitor;
   a polymerase inhibitor;
   one or more anti-fibrotic and/or anti-hemolytic agents comprising one or more Polyphenols and/or one or more Thiols; and
   one or more non-anticoagulant glycosaminoglycans (GAGs).

2. The composition of claim 1, wherein the protease inhibitor is 1-[(2R,3R,4S,5R)-3,4-dihydroxy-5-(hydroxymethyl)oxolan-2-yl]-1H-1,2,4-triazole-3-carbox.

3. The composition of claim 1, wherein the Nanoformulation includes Galactosylated Solid Lipid Nanoparticles (SLN), with targeting to hepatitis C virus (HCV) and/or the liver.

4. The composition of claim 1, wherein the Nanoformulation includes Chitosan cross-linked with alginate or Chitosan cross-linked with Hyaluronic acid, with targeting to hepatitis C virus (HCV) and/or the liver.

5. The composition of claim 1, wherein the polymerase inhibitor is Sofosbuvir.

6. The composition of claim 1, wherein the one or more anti-fibrotic and/or anti-hemolytic agents comprise epigallocatechin gallate (EGCG) and/or N-acetyl Cysteine.

7. The composition of claim 1, wherein the non-anticoagulant GAGs comprise sulfated Oligosaccharide with a molecular weight of 4,000-6,000 Daltons.

8. The composition of claim 1, wherein the one or more Polyphenols and/or one or more Thiols are derived from natural sources.

9. A method of treating a hepatitis C virus (HCV) infection in an animal, comprising:
   administering to the animal a therapeutic dose of the composition of claim 1 to treat the animal for the HCV infection.

10. The method of claim 9, wherein the animal is a human being.

11. A composition, comprising:
   ribavirin or taribavirin;
   a polymerase inhibitor;
   one or more anti-fibrotic and/or anti-hemolytic agents comprising one or more Polyphenols and/or one or more Thiols; and
   one or more non-anticoagulant glycosaminoglycans (GAGs).

12. The composition of claim 11, wherein the composition comprises the ribavirin.

13. The composition of claim 11, wherein the polymerase inhibitor is Sofosbuvir.

14. The composition of claim 11, wherein the one or more anti-fibrotic and/or anti-hemolytic agents comprise epigallocatechin gallate (EGCG) and/or N-acetyl Cysteine.

15. A method of treating a hepatitis C virus (HCV) infection in an animal, comprising:
   administering to the animal a therapeutic dose of the composition of claim 11 to treat the animal for the HCV infection.

16. The method of claim 15, wherein the animal is a human being.

17. A composition, comprising:
   ribavirin or taribavirin;
   a polymerase inhibitor; and
   one or more anti-fibrotic and/or anti-hemolytic agents comprising one or more Polyphenols and/or one or more Thiols,
      wherein the composition comprises a Nanoformulation that includes the ribavirin or taribavirin, the polymerase inhibitor, and the anti-fibrotic and/or anti-hemolytic agents.

18. The composition of claim 17, wherein the Nanoformulation includes Galactosylated Solid Lipid Nanoparticles (SLN), with targeting to hepatitis C virus (HCV) and/or the liver.

19. The composition of claim 17, wherein the Nanoformulation includes Chitosan cross-linked with alginate or Chitosan cross-linked with Hyaluronic acid, with targeting to hepatitis C virus (HCV) and/or the liver.

20. The composition of claim 17, further comprising:
   one or more non-anticoagulant glycosaminoglycans (GAGs).

21. A method of treating a hepatitis C virus (HCV) infection in a human being, comprising:
   administering to the human being a therapeutic dose of the composition of claim 17 to treat the human being for the HCV infection.

* * * * *